(12) United States Patent
Hattori et al.

(10) Patent No.: US 6,851,180 B2
(45) Date of Patent: Feb. 8, 2005

(54) METHOD OF MANUFACTURING A GAS SENSOR

(75) Inventors: Yasuo Hattori, Kuwana (JP); Kazuo Matsubara, Kuwana (JP)

(73) Assignee: Denso Corporation, Kariya (JP)

( * ) Notice: Subject to any disclaimer, the term of this patent is extended or adjusted under 35 U.S.C. 154(b) by 172 days.

(21) Appl. No.: 10/109,052

(22) Filed: Mar. 29, 2002

(65) Prior Publication Data

US 2002/0138967 A1 Oct. 3, 2002

(30) Foreign Application Priority Data

Mar. 29, 2001 (JP) .................................. 2001-096594

(51) Int. Cl.[7] .............................................. H01C 17/28
(52) U.S. Cl. ..................... 29/619; 29/90.7; 29/592.1; 29/593; 29/595; 29/DIG. 36; 73/23.31; 73/31.05; 204/424; 204/427
(58) Field of Search ..................... 29/619, 90.7, 592.1, 29/593, 595, DIG. 36; 73/23.31, 31.05; 204/424, 427

(56) References Cited

U.S. PATENT DOCUMENTS

| 5,679,226 A | * 10/1997 | Furusaki et al. ............. 204/424 |
| 6,082,175 A | * 7/2000 | Yoshikawa et al. ......... 73/23.31 |
| 6,383,353 B1 | * 5/2002 | Akatsuka et al. ........... 204/424 |

FOREIGN PATENT DOCUMENTS

| EP | 0932039 A2 | 7/1999 |
| EP | 0939314 A2 | 9/1999 |
| EP | 0979996 A2 | 2/2000 |
| JP | 6-3430 | 1/1994 |
| WO | WO 98/38505 | 9/1998 |

* cited by examiner

*Primary Examiner*—Carl J. Arbes
*Assistant Examiner*—Tim Phan
(74) *Attorney, Agent, or Firm*—Nixon & Vanderhye P.C.

(57) ABSTRACT

A manufacturing method for a gas senor having sensor element on and in which an outer electrode terminal and an inner electrode terminal are press-fitted. The manufacturing method features stability of installation of the outer and inner electrode terminals without causing physical damage to the sensor element. Outer and inner terminal installation jigs are used in the method.

7 Claims, 17 Drawing Sheets

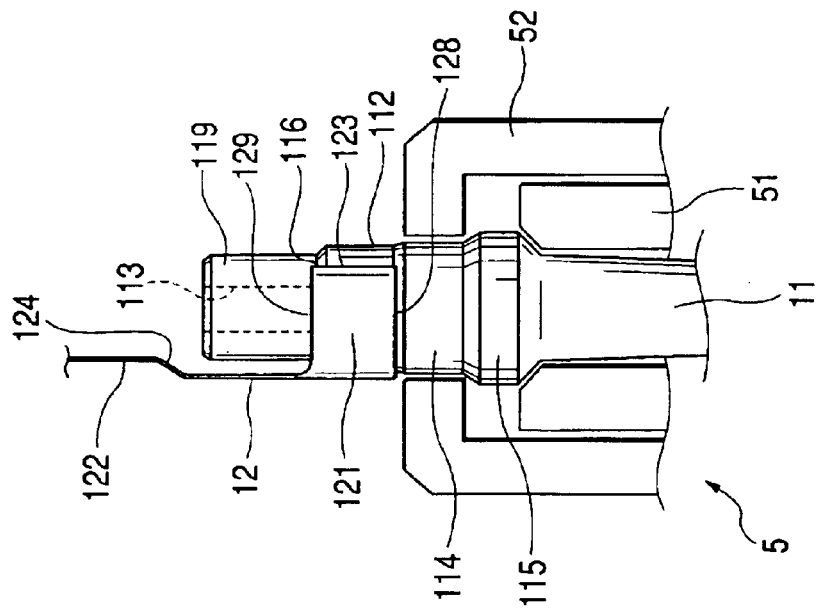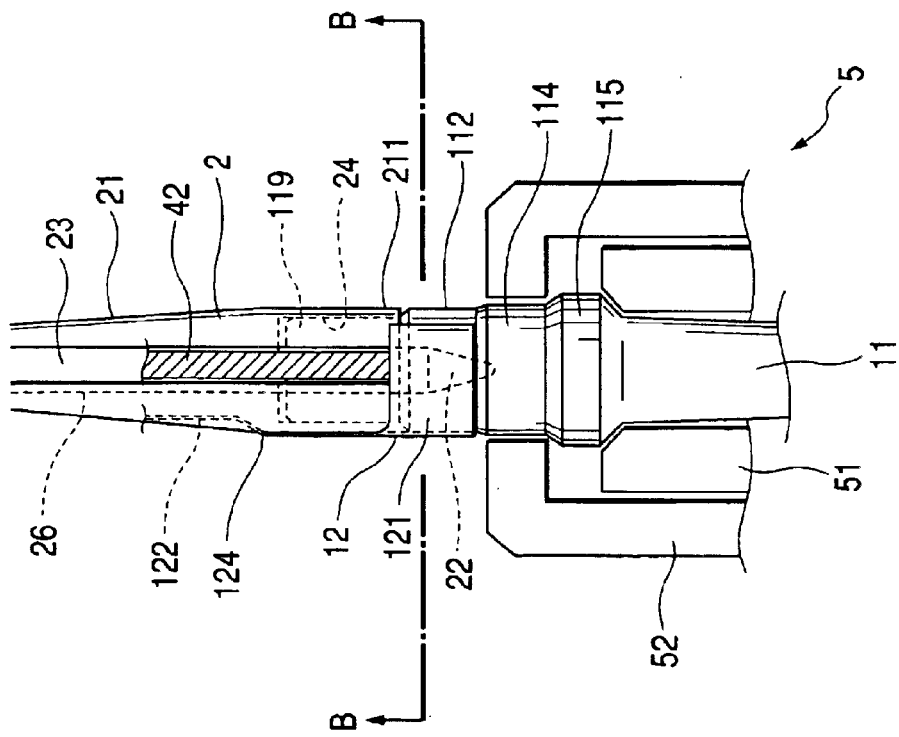

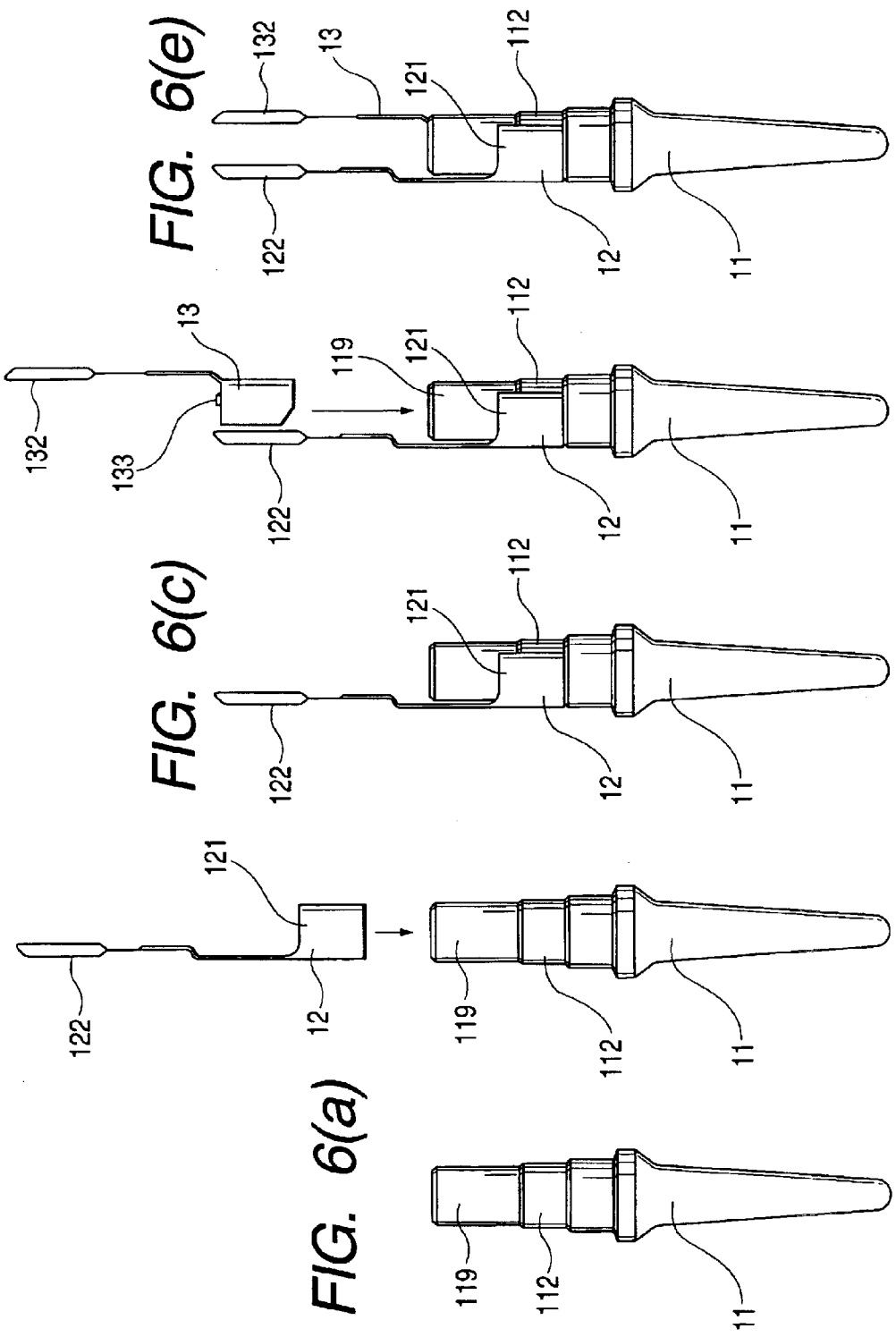

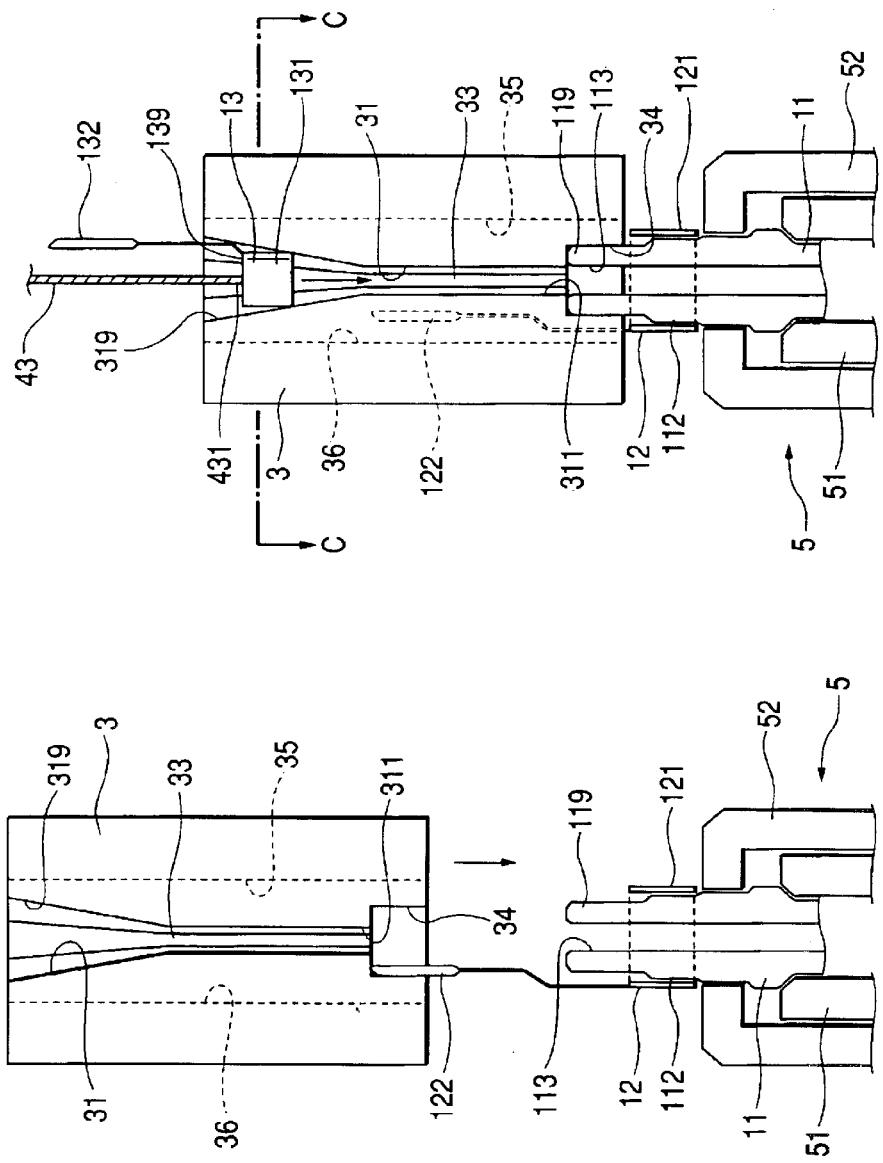

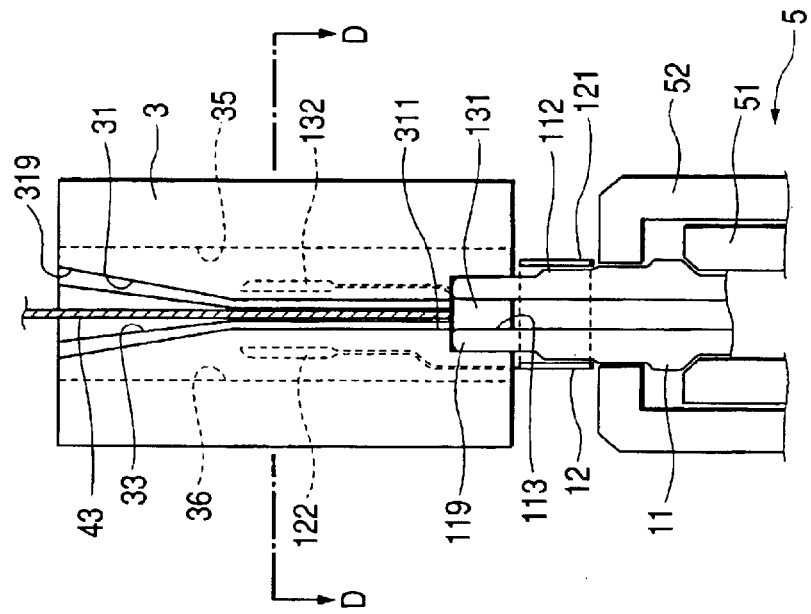
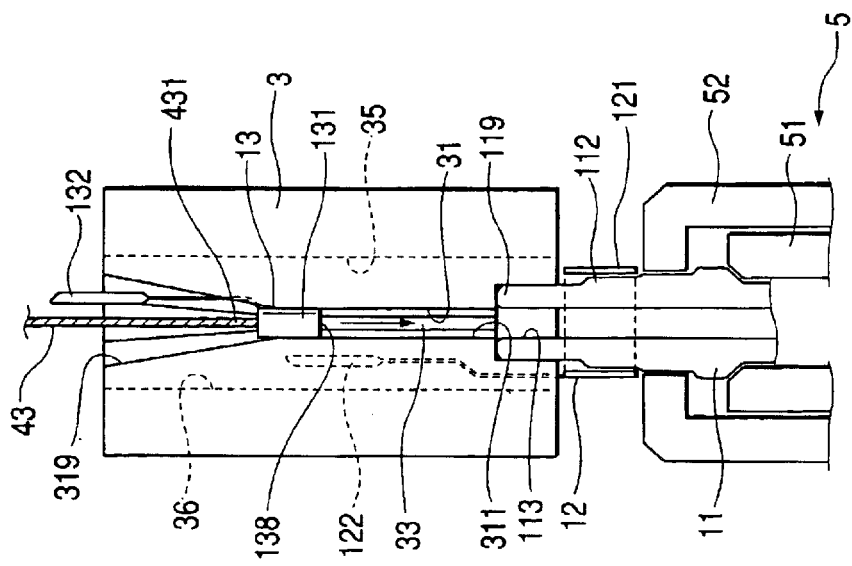

METHOD OF MANUFACTURING A GAS SENSOR

CROSS REFERENCE TO RELATED DOCUMENT

The present application claims the benefit of Japanese Application, JAPAN 2001-96594, which was filed on $29^{th}$ Mar. 2001."

BACKGROUND OF THE INVENTION

1. Technical Field of the Invention

The present invention relates generally to a manufacturing method of a sensor element of a gas sensor provided with an electrode terminal and a terminal installation jig used to install the electrode terminal on the sensor element without causing any damage to the sensor element.

2. Background Art

Japanese Patent Second Publication No. 6-3430 discloses a typical gas sensor consisting of a hollow cylindrical sensor element and an inner electrode installed in the sensor element. The inner electrode terminal is made up of an annular holder and a lead extending from the annular holder. The annular holder is connected electrically with one of electrodes installed in the sensor element. The lead is connected electrically with an external device.

The annular holder has an outer diameter greater than an inner diameter of the inner terminal mount and is press-fitted to an inner terminal mount formed on an inner surface of the sensor element. The installation of the inner electrode terminal is achieved by compressing the annular holder inwardly and inserting it into an end opening of the sensor element.

It is, however, relatively difficult to compress the annular holder to decrease the outer diameter thereof to the degree required for insertion into the end opening of the sensor element. A failure in such compression may result in collision of the annular holder with the end of the sensor element, which causes the damage to the sensor element. The same applies to the outer electrode holder.

SUMMARY OF THE INVENTION

It is therefore a principal object of the invention to avoid the disadvantages of the prior art.

It is another object of the invention to provide a manufacturing method of a gas sensor which is capable of assembling the gas sensor without causing physical damage to a sensor element and which is excellent in productivity;

It is a further object of the invention to provide a terminal installation jig used in installing an electrode terminal on a sensor element of a gas sensor.

According to one aspect of the invention, there is provided a manufacturing method of manufacturing a gas sensor which includes (a) a hollow cylindrical sensor element of a given length having a first and a second end portion opposed to each other, (b) an outer electrode terminal installed on an outer terminal mount formed on an outer peripheral surface of the second end portion of the cylindrical sensor element, and (c) an inner electrode terminal installed on an inner terminal mount formed on an inner peripheral surface of the second end portion of the cylindrical sensor element. The gas sensor may be used in measuring the concentration of oxygen contained in exhaust gasses of an automotive internal combustion engines. The manufacturing method features installation of the outer electrode terminal on the sensor element without causing any physical damage to the sensor element. The manufacturing method comprises the steps of: (a) preparing the outer electrode terminal made up of an elastically deformable annular holder and a lead extending from the annular holder, the annular holder having an inner diameter smaller than an outer diameter of the outer terminal mount of the cylindrical sensor element; (b) preparing an outer terminal installation jig of a given length which has a first and a second end opposed to each other and a skirt with an outer wall tapering off to the second end, an outer diameter of the first end being greater than or equal to the outer diameter of the outer terminal mount of the sensor element; (c) placing the outer terminal installation jig at the first end thereof on the second end portion of the sensor element; (d) placing the annular holder of the outer electrode terminal on the skirt of the outer terminal installation jig; (e) moving the annular holder toward the first end of the outer installation terminal jig along the tapered outer wall of the skirt to increase the inner diameter of the annular holder and placing the annular holder at the outer terminal mount of the sensor element; (f) removing the outer terminal installation jig from the annular holder of the outer electrode terminal to establish tight engagement of the annular holder with the outer terminal mount of the sensor element; and (g) installing the inner electrode terminal on the inner terminal mount.

In the preferred mode of the invention, the outer terminal installation jig includes a central positioning pin which is disposed in the skirt along a longitudinal center line of the skirt and partially projects from the fist end of the outer terminal installation jig. The outer terminal installation jig placing step inserts the central positioning pin into the second end portion of the sensor element to align the outer terminal installation jig with the sensor element.

According to the second aspect of the invention, there is provided a manufacturing method of a gas sensor including (a) a hollow cylindrical sensor element of a given length having a first and a second end portion opposed to each other and (b) an inner electrode terminal installed on an inner terminal mount formed on an inner peripheral surface of the second end portion of the cylindrical sensor element. The manufacturing method features the stability of installation of the inner electrode terminal in the sensor element without causing any physical damage to the sensor element. The manufacturing method comprises the steps of: (a) preparing the inner electrode terminal made up of an elastically deformable annular holder, a lead, and a protrusion, the annular holder having an outer diameter greater than an inner diameter of the inner terminal mount of the cylindrical sensor element and a first and a second end opposed to each other, the lead extending from the second end of the annular holder, the protrusion projecting from the second end of the annular holder outward; and (b) inserting the annular holder of the inner electrode terminal at the first end thereof into the second end portion of the cylindrical sensor element until a given clearance is formed between the protrusion and an end surface of the second end portion of the cylindrical sensor element to install the inner electrode terminal on the inner terminal mount of the sensor element.

According to the third aspect of the invention, there is provided a manufacturing method of a gas sensor including (a) a hollow cylindrical sensor element of a given length having a first and a second end portion opposed to each other and (b) an outer electrode terminal installed on an outer terminal mount formed on an outer peripheral surface of the second end portion of the cylindrical sensor element. The manufacturing method features use of a press device for providing the stability of the outer electrode terminal on the sensor element. The manufacturing method comprises the steps of: (a) preparing the outer electrode terminal made up of an elastically deformable annular holder having a first and a second end opposed to each other and a lead extending from the second end of the annular holder, the annular holder having an inner diameter smaller than an outer diameter of the outer terminal mount of the cylindrical sensor element; (b) preparing an outer terminal installation jig of a given length which has a first and a second end opposed to each other and a skirt with an outer wall tapering off to the second end, an outer diameter of the first end being greater than or equal to the outer diameter of the outer terminal mount of the sensor element; (c) placing the outer terminal installation jig at the first end thereof on the second end portion of the sensor element; (d) placing the annular holder of the outer electrode terminal on the skirt of the outer terminal installation jig; (e) placing press members in contact with a plurality of portions of the second end of the annular holder of the outer electrode terminal; (f) thrusting the press members toward the first end of the outer installation terminal jig to move the annular holder of the outer electrode terminal along the tapered outer wall of the skirt to increase the inner diameter of the annular holder and placing the annular holder at the outer terminal mount of the sensor element; and (g) removing the outer terminal installation jig from the annular holder of the outer electrode terminal to establish tight engagement of the annular holder with the outer terminal mount of the sensor element.

In the preferred mode of the invention, the skirt of the outer terminal installation jig has a plurality of slide guide grooves formed in an outer surface thereof which extend in a lengthwise direction of the outer terminal installation jig to guide sliding movement of the press members to thrust the annular holder of the outer electrode terminal to the first end from the second end of the outer terminal installation jig.

The outer terminal installation jig includes a central positioning pin which is disposed in the skirt along a longitudinal center line of the skirt and partially projects from the fist end of the outer terminal installation jig. The outer terminal installation jig placing step inserts the central positioning pin into the second end portion of the sensor element to align the outer terminal installation jig with the sensor element.

According to the fourth aspect of the invention, there is provided a manufacturing method of a gas sensor including (a) a hollow cylindrical sensor element of a given length having a first and a second end portion opposed to each other and (b) an inner electrode terminal installed on an inner terminal mount formed on an inner peripheral surface of the second end portion of the cylindrical sensor element. The manufacturing method features use of a press device for providing the stability of the inner electrode terminal in the sensor element. The manufacturing method comprises the steps of: (a) preparing the inner electrode terminal made up of an elastically deformable annular holder and a lead, the annular holder having an outer diameter greater than an inner diameter of the inner terminal mount of the cylindrical sensor element and a first and a second end opposed to each other, the lead extending from the second end of the annular holder; (b) preparing an inner terminal installation jig of a given length which has a first and a second end opposed to each other and a through hole tapering off to the first end, an inner diameter of an opening of the through hole formed in the first end being smaller than or equal to the inner diameter of the inner terminal mount of the sensor element; (c) placing the inner terminal installation jig at the first end thereof on the second end portion of the sensor element; (d) placing the annular holder of the inner electrode terminal in the through hole of the inner terminal installation jig; (e) placing press members in contact with a plurality of portions of the second end of the annular holder of the inner electrode terminal; (f) thrusting the press members toward the first end of the inner installation terminal jig to move the annular holder of the inner electrode terminal through the through hole to decrease the outer diameter of the annular holder and placing the annular holder at the inner terminal mount of the sensor element; and (g) removing the inner terminal installation jig from the annular holder of the inner electrode terminal to establish tight engagement of the annular holder with the inner terminal mount of the sensor element.

In the preferred mode of the invention, the inner terminal installation jig has a plurality of slide guide grooves formed in an inner surface thereof which extend in a lengthwise direction of the inner terminal installation jig to guide sliding movement of the press members to thrust the annular holder of the inner electrode terminal to the first end from the second end of the inner terminal installation jig.

The inner electrode terminal has a protrusion projecting from the second end of the annular holder outward. The thrusting step moves the annular holder of the inner electrode terminal through the through hole until a given clearance is formed between the protrusion and an end surface of the second end portion of the cylindrical sensor element to install the inner electrode terminal on the inner terminal mount of the sensor element.

According to the fifth aspect of the invention, there is provided a manufacturing method of a gas sensor including (a) a hollow cylindrical sensor element of a given length having a first and a second end portion opposed to each other, (b) an outer electrode terminal installed on an outer terminal mount formed on an outer peripheral surface of the second end portion of the cylindrical sensor element, and (c) an inner electrode terminal installed on an inner terminal mount formed on an inner peripheral surface of the second end portion of the cylindrical sensor element. The manufacturing method features the stability of installation of the outer and inner electrode terminal on and in the sensor element without causing any physical damage to the sensor element. The manufacturing method comprises the steps of: (a) preparing the outer electrode terminal made up of an elastically deformable annular holder and a lead extending from the annular holder, the annular holder having an inner diameter smaller than an outer diameter of the outer terminal mount of the cylindrical sensor element; (b) preparing an outer terminal installation jig of a given length which has a first and a second end opposed to each other and a skirt with an outer wall tapering off to the second end, an outer diameter of the first end being greater than or equal to the outer diameter of the outer terminal mount of the sensor element; (c) placing the outer terminal installation jig at the first end thereof on the second end portion of the sensor element; (d) placing the annular holder of the outer electrode terminal on the skirt of the outer terminal installation jig; (e) placing press members in contact with a plurality of portions of the second end of the annular holder of the outer electrode terminal; (f) thrusting the press members toward the first end of the outer installation terminal jig to move the annular holder of the outer electrode terminal along the tapered outer wall of the skirt to increase the inner diameter of the annular holder and placing the annular holder at the outer terminal mount of the sensor element; (g) removing the outer terminal installation jig from the annular holder of the outer electrode terminal to establish tight engagement of the annular holder with the outer terminal mount of the sensor element; (h) preparing the inner electrode terminal made up of an elastically deformable annular holder, a lead, and a protrusion, the annular holder having an outer diameter greater than an inner diameter of the inner terminal mount of the cylindrical sensor element and a first and a second end opposed to each other, the lead extending from the second end of the annular holder, the protrusion projecting from the second end of the annular holder outward; (i) preparing an inner terminal installation jig of a given length which has a first and a second end opposed to each other and a through hole tapering off to the first end, an inner diameter of an opening of the through hole formed in the first end being smaller than or equal to the inner diameter of the inner terminal mount of the sensor element; (j) after removing the outer terminal installation jig from the annular holder of the outer electrode terminal, placing the inner terminal installation jig at the first end thereof on the second end portion of the sensor element; (k) placing the annular holder of the inner electrode terminal in the through hole of the inner terminal installation jig; (l) placing press members in contact with a plurality of portions of the second end of the annular holder of the inner electrode terminal; (m) thrusting the press members toward the first end of the inner installation terminal jig to move the annular holder of the inner electrode terminal through the through hole to decrease the outer diameter of the annular holder and placing the annular holder at the inner terminal mount of the sensor element; and (n) removing the inner terminal installation jig from the annular holder of the inner electrode terminal to establish tight engagement of the annular holder with the inner terminal mount of the sensor element.

According to the sixth aspect of the invention, there is provided an outer terminal installation jig used to install an outer electrode terminal on an outer terminal mount formed on an outer peripheral surface of a cylindrical sensor element of a gas sensor. The outer electrode terminal has an annular holder whose inner diameter is smaller than an outer diameter of the outer terminal mount. The outer terminal installation jig is designed to provide the stability of installation of the outer electrode terminal on the sensor element and comprises: (a) a cylindrical member of a given length which has a first and a second end opposed to each other and a skirt, the skirt having an outer wall tapering off to the second end, an outer diameter of the first end being greater than or equal to the outer diameter of the outer terminal mount of the sensor element, an outer diameter of the second end being smaller than an inner diameter of the annular holder before installed on the cylindrical sensor element; and (b) a recess formed in the first end of the cylindrical member. The recess is configured to establish engagement of the cylindrical member with an end of the cylindrical sensor element for installing the outer electrode terminal on the outer terminal mount of the cylindrical sensor element.

In the preferred mode of the invention, the outer terminal installation jig further comprises a central positioning pin which is disposed in the skirt along a longitudinal center line of the cylindrical member and partially projects from the fist end of the cylindrical member for insertion into the end of the sensor element to align the cylindrical member with the sensor element.

The outer terminal installation jig may also includes a turn stopper which projects outwardly from the skirt of the cylindrical member and works to engage a slit formed in the annular holder of the outer electrode terminal for holding the annular holder from turning when the annular holder is installed on the outer terminal mount of the sensor element.

The outer electrode terminal has a lead extending from the annular holder. The skirt may have a guide groove formed in an outer surface thereof which extends in the lengthwise direction of the cylindrical member for guiding sliding movement of the lead of the outer electrode terminal when the annular holder of the outer electrode terminal is thrust along the skirt of the cylindrical member from the second end to the first end of the cylindrical member and installed on the outer terminal mount of the sensor element.

The skirt of the cylindrical member may have a plurality of slide guide grooves formed in an outer surface thereof which extend in the lengthwise direction of the cylindrical member for guiding sliding movement of press members used to thrust the annular holder of the outer electrode terminal to the first end from the second end of the cylindrical member.

According to the seventh aspect of the invention, there is provided an inner terminal installation jig used to install an inner electrode terminal on an inner terminal mount formed on an inner peripheral surface of a hollow cylindrical sensor element of a gas sensor. The inner terminal has an annular holder whose outer diameter is greater than an inner diameter of the inner terminal mount. The inner terminal installation jig is designed to provide the stability of installation of the inner electrode terminal on the sensor element and comprises: (a) a member of a given length which has a first and a second end opposed to each other and a through hole extending from the first to the second end, the through hole tapering off to the first end, an inner diameter of an opening of the through hole formed in the first end being smaller than or equal to the inner diameter of the inner terminal mount of the sensor element, an outer diameter of an opening of the through hole formed in the second end being greater than an outer diameter of the annular holder of the inner electrode terminal before installed in the cylindrical sensor element; and (b) a recess formed in the first end of the member in communication with the through hole. The recess is configured to establish engagement of the member with an end of the cylindrical sensor element for installing the inner electrode terminal on the inner terminal mount of the cylindrical sensor element.

In the preferred mode of the invention, the inner electrode terminal has a lead extending from the annular holder. The through hole may have a guide groove formed in an inner surface of the member which extends in a lengthwise direction of the member for guiding sliding movement of the lead of the inner electrode terminal when the annular holder of the inner electrode terminal is thrust through the through hole from the second end to the first end of the member and installed on the inner terminal mount of the sensor element.

The inner electrode terminal may also have a protrusion projecting from the annular holder. The through hole may have a guide groove formed in an inner surface of the member which extends in a lengthwise direction of the member for guiding sliding movement of the protrusion of the inner electrode terminal when the annular holder of the inner electrode terminal is thrust through the through hole from the second end to the first end of the member and installed on the inner terminal mount of the sensor element.

The through hole may have a plurality of slide guide grooves formed in an inner surface thereof which extend in the lengthwise direction of the member for guiding sliding movement of press members used to thrust the annular holder of the inner electrode terminal to the first end from the second end of the member within the through hole.

The through hole may have a storage groove formed in an inner surface of the member which extends in a lengthwise direction of the member and in which a lead of an outer electrode terminal mounted on an outer terminal mount of the sensor element is stored for avoiding physical interference of the member with the lead of the outer electrode terminal when the member is disposed on the end of the sensor element.

According to the eighth aspect of the invention, there is provided an outer terminal installation jig used to install an outer electrode terminal on an outer terminal mount formed on an outer peripheral surface of a cylindrical sensor element of a gas sensor, the outer electrode terminal having an annular holder whose inner diameter is smaller than an outer diameter of the outer terminal mount. The outer terminal installation jig comprises: (a) a cylindrical member of a given length which has a first and a second end opposed to each other and a skirt; and (b) a central positioning pin. The skirt has an outer wall tapering off to the second end. The outer diameter of the first end is greater than or equal to the outer diameter of the outer terminal mount of the sensor element. The outer diameter of the second end is smaller than an inner diameter of the annular holder before installed on the cylindrical sensor element. The central positioning pin is disposed in the skirt in alignment with a longitudinal center line of the cylindrical member and partially projects from the fist end of the cylindrical member for insertion into the end of the sensor element to align the cylindrical member with the sensor element.

In the preferred mode of the invention, the outer terminal installation jig further includes a turn stopper which projects outwardly from the skirt of the cylindrical member and works to engage a slit formed in the annular holder of the outer electrode terminal for holding the annular holder from turning when the annular holder is installed on the outer terminal mount of the sensor element.

The outer electrode terminal has a lead extending from the annular holder. The skirt has a guide groove formed in an outer surface thereof which extends in a lengthwise direction of the cylindrical member for guiding sliding movement of the lead of the outer electrode terminal when the annular holder of the outer electrode terminal is thrust along the skirt of the cylindrical member from the second end to the first end of the cylindrical member and installed on the outer terminal mount of the sensor element.

The skirt of the cylindrical member has a plurality of slide guide grooves formed in an outer surface thereof which extend in a lengthwise direction of the cylindrical member for guiding sliding movement of press members used to thrust the annular holder of the outer electrode terminal to the first end from the second end of the cylindrical member.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

Figure 3A:
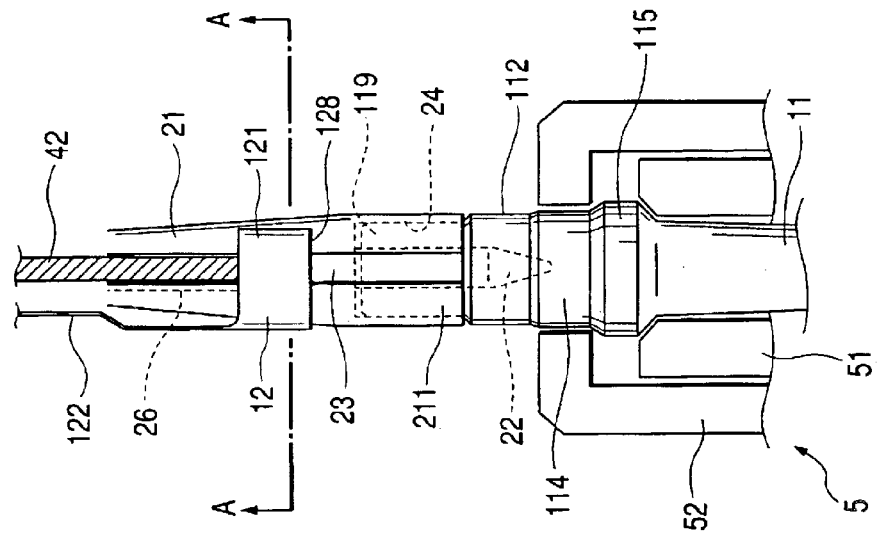
Figure 3B:
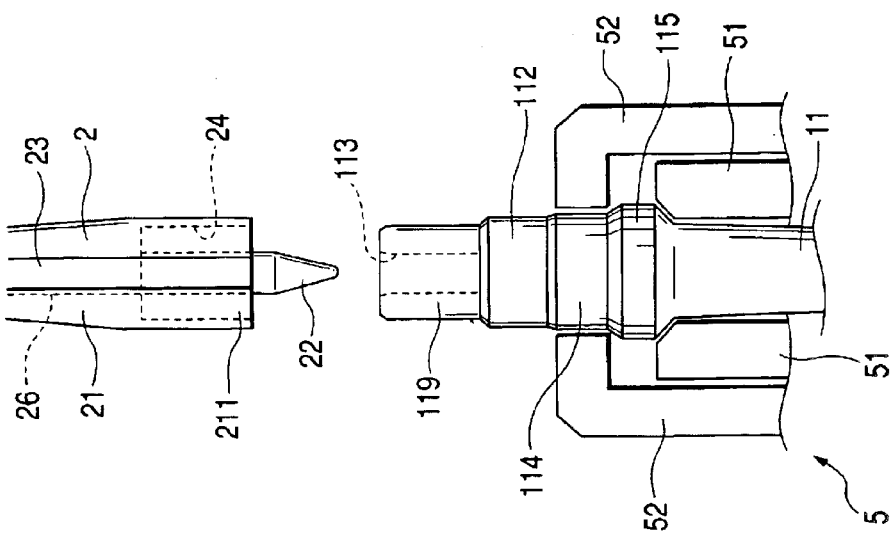
Figure 5:
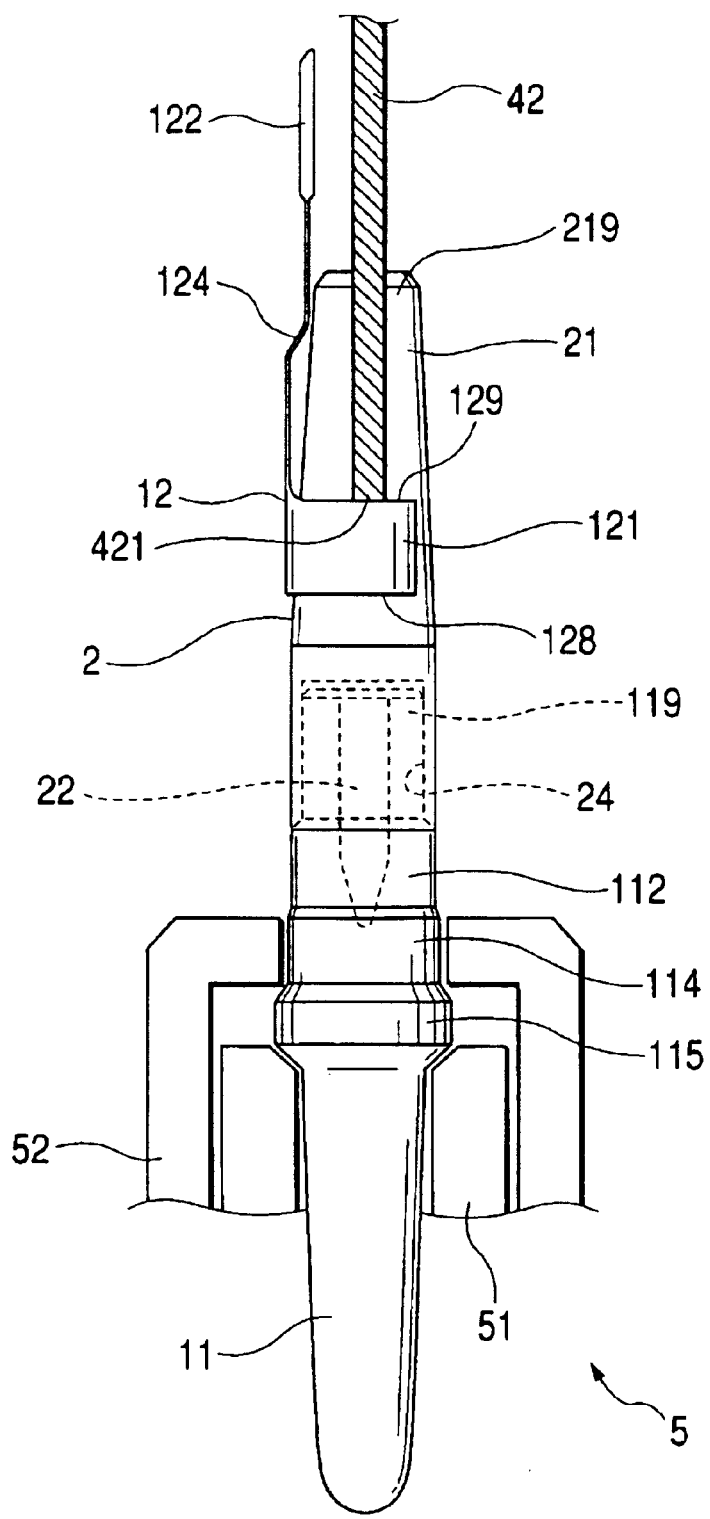
Figure 7A:
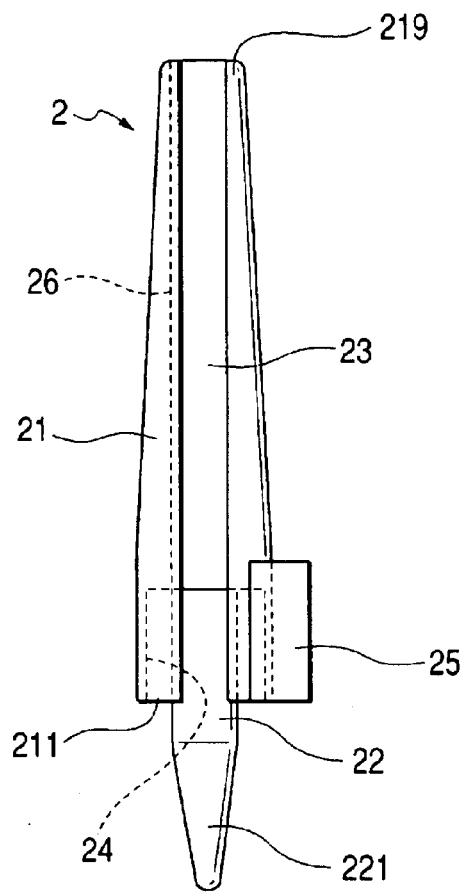
Figure 7B:
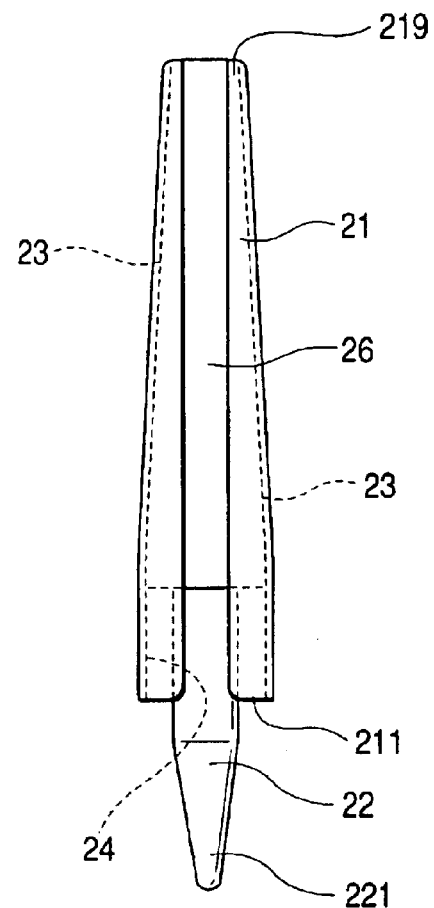
Figure 8A:
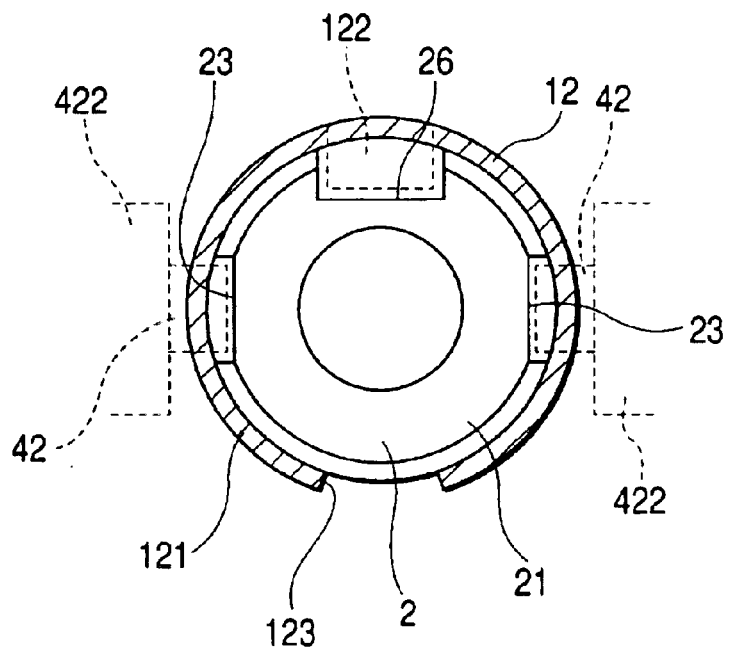
Figure 8B:
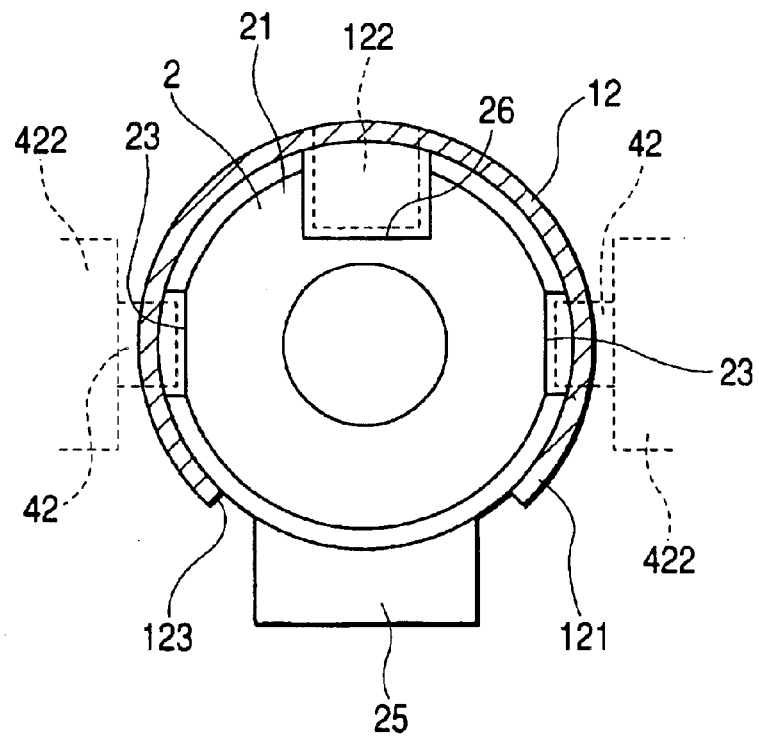
Figure 9:
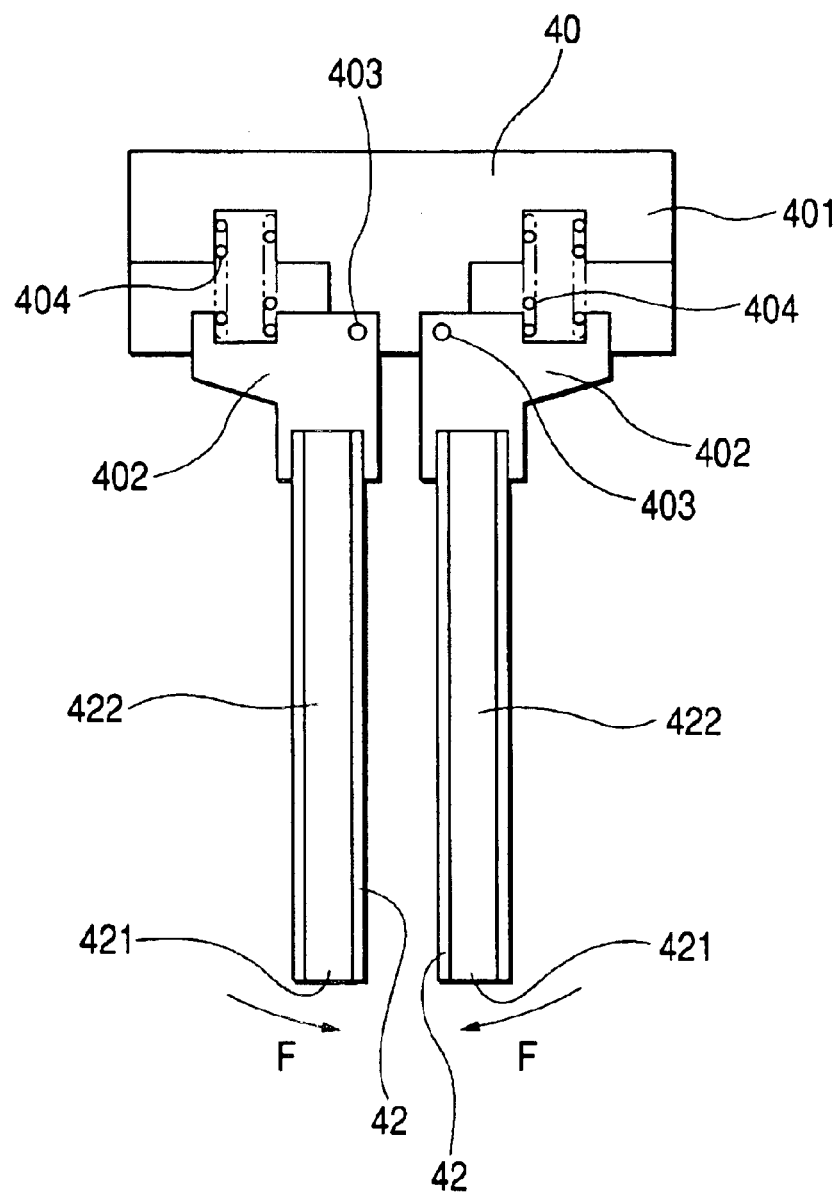
Figure 10:
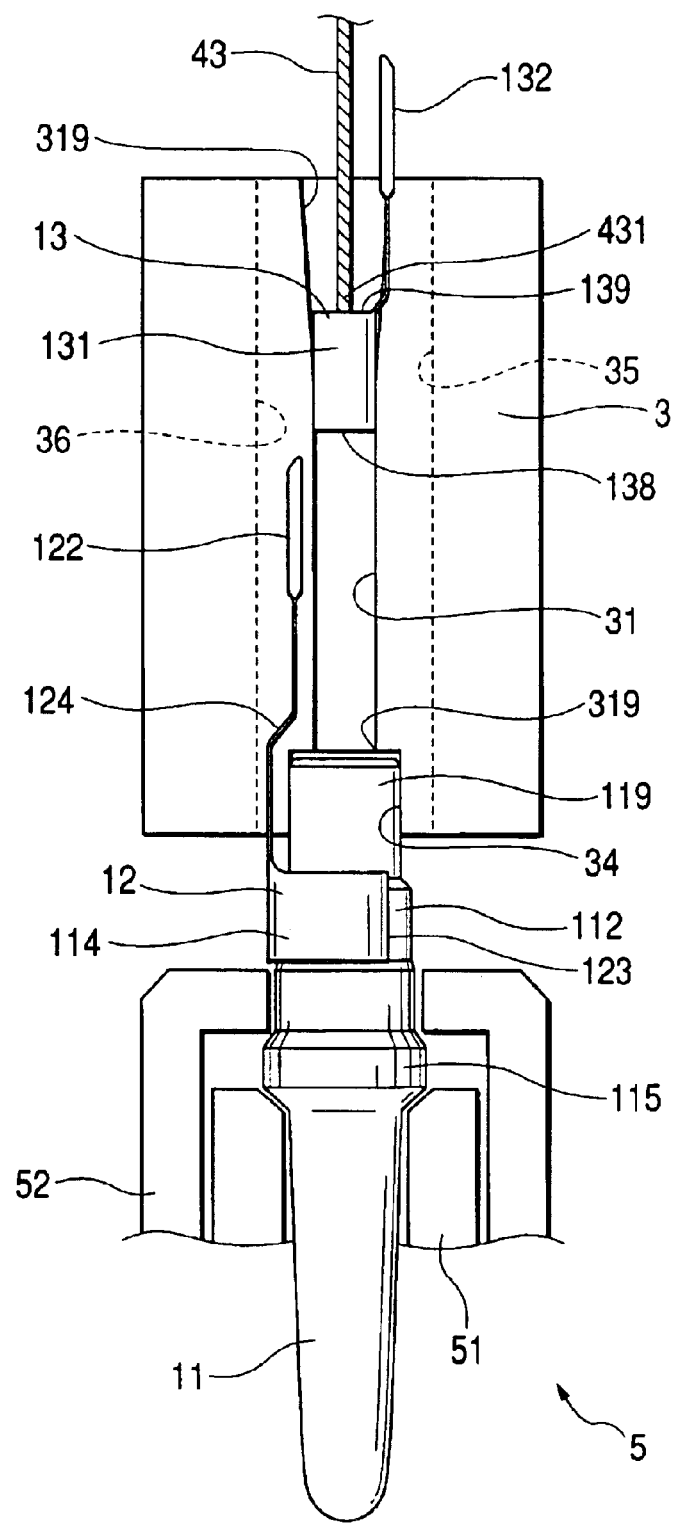
Figure 13A:
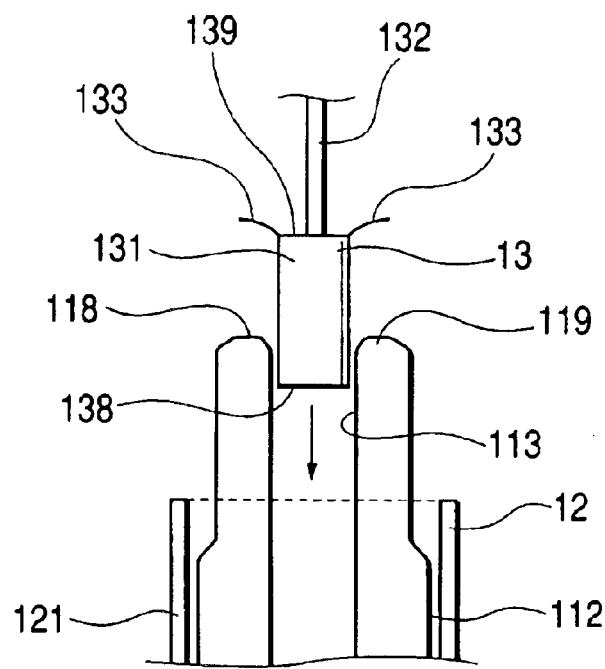
Figure 13B:
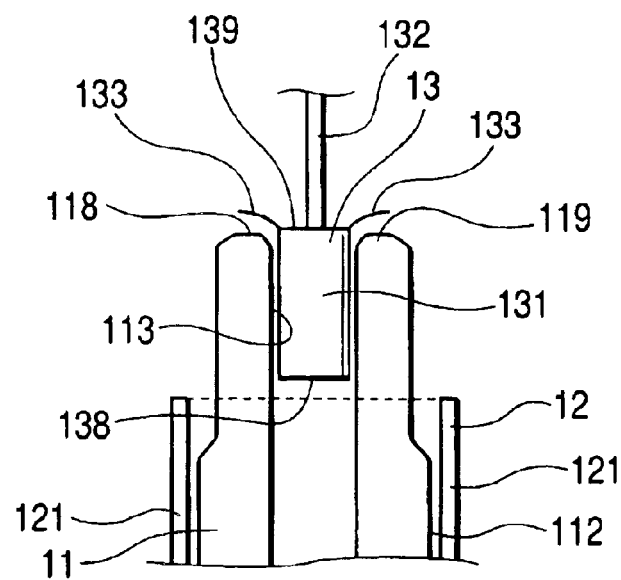
Figure 14A:
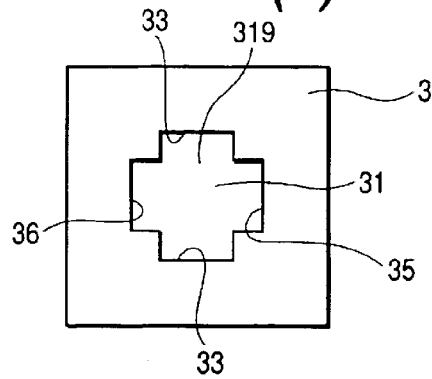
Figure 14B:
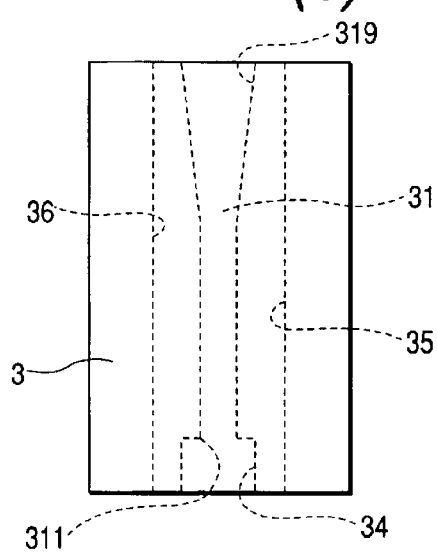
Figure 14D:
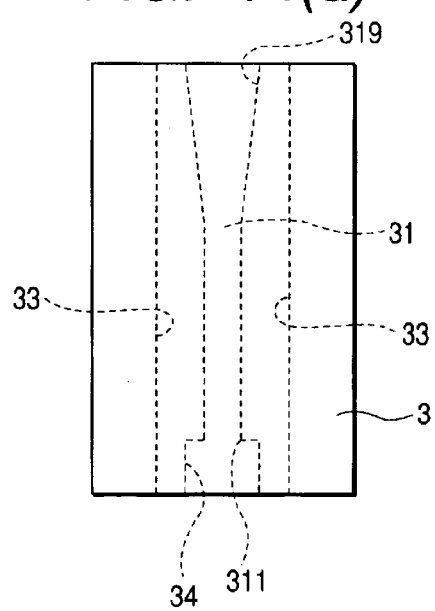
Figure 14C:
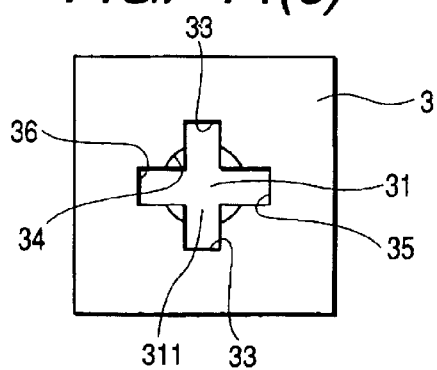
Figure 15A:
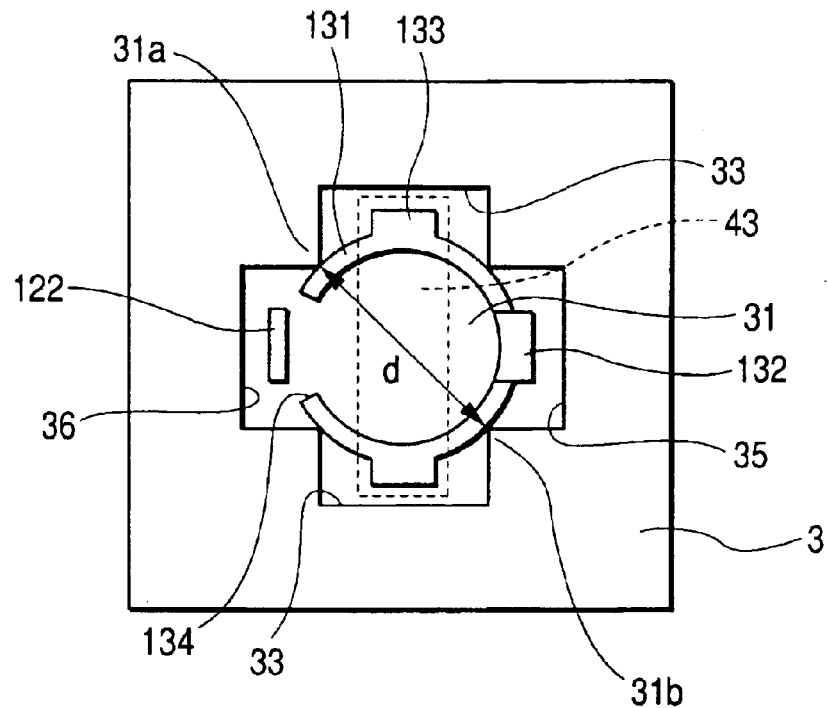
Figure 15B:
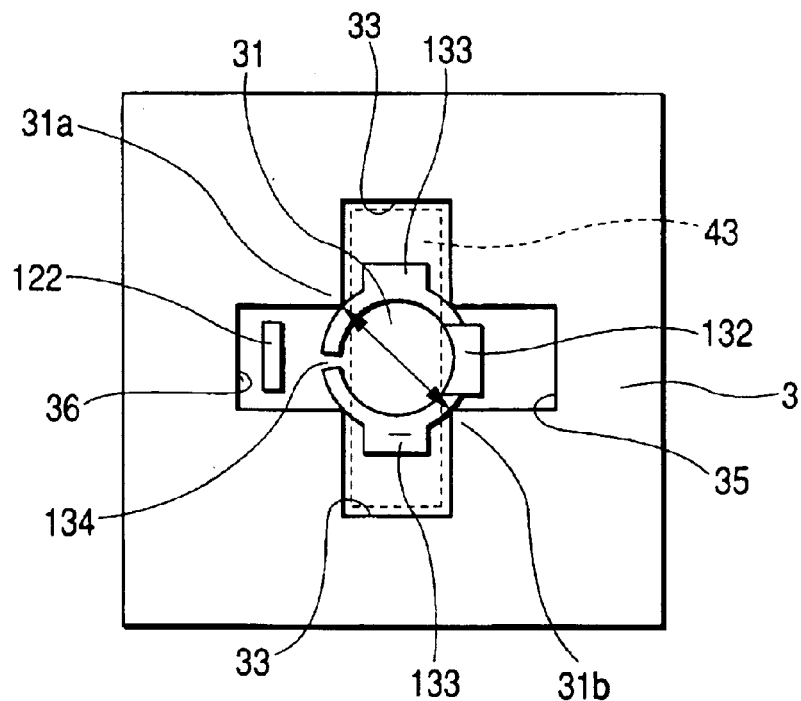
Figure 16A:
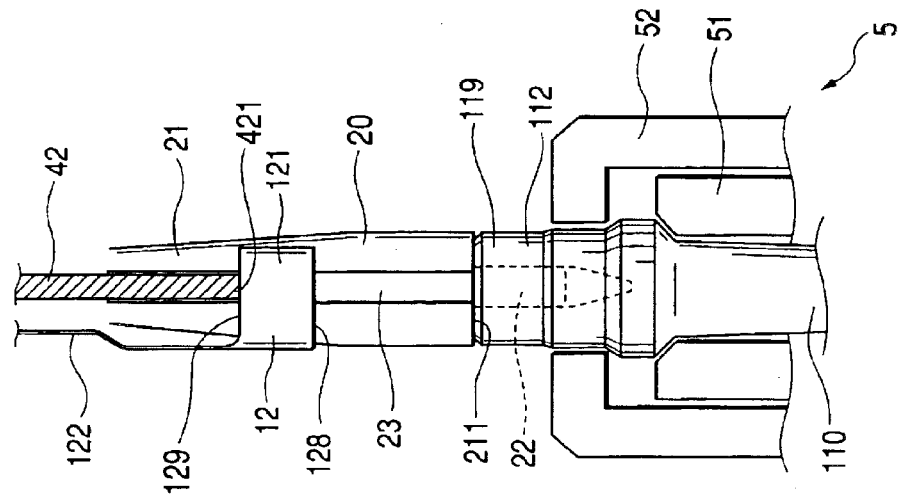
Figure 16B:
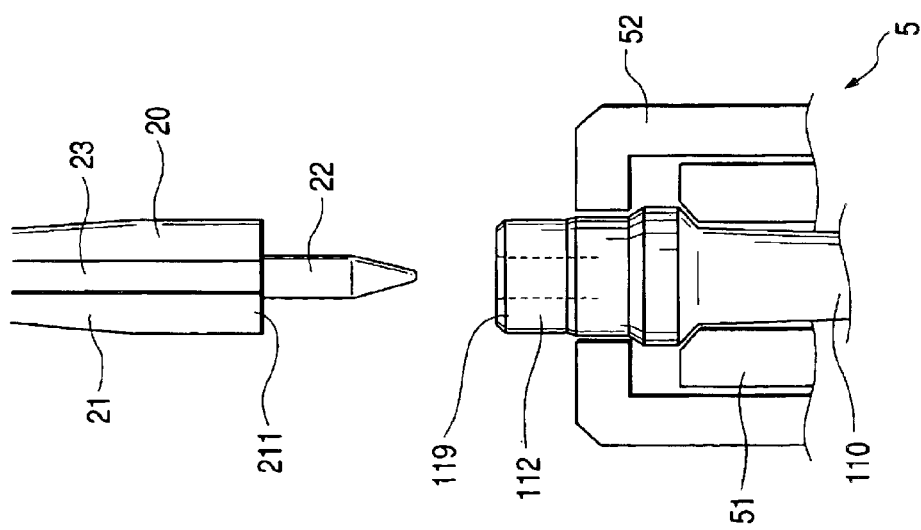
Figure 17:
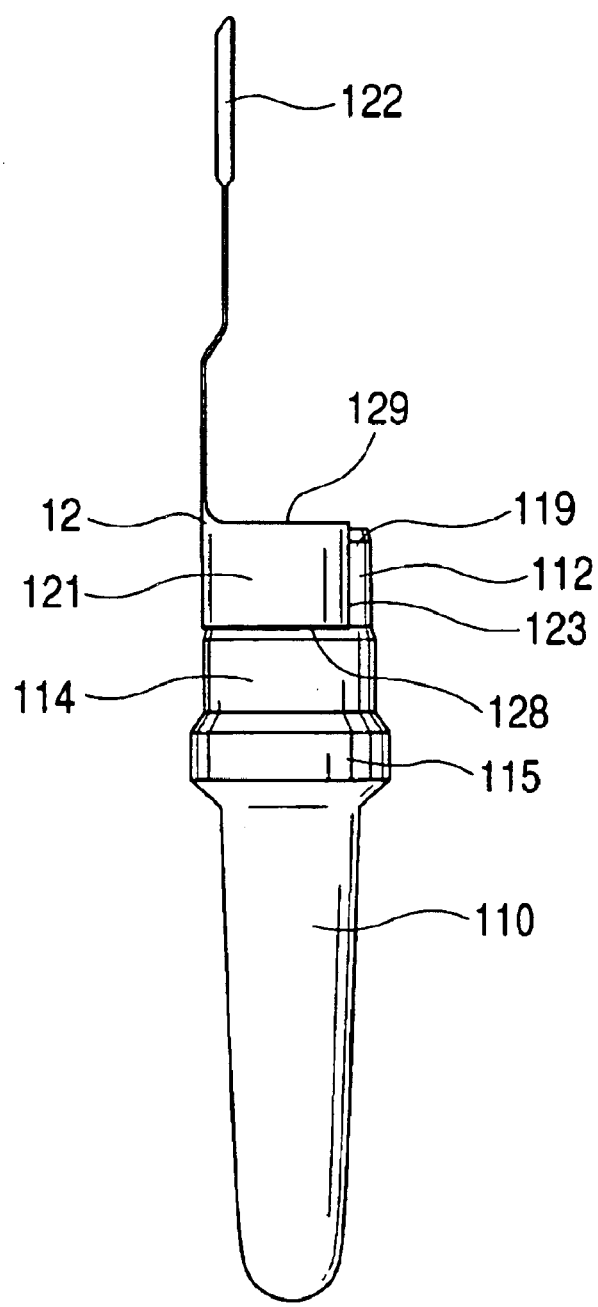

FIGS. 3(a), 3(b), 4(a), and 4(b) show a sequence of installation steps of fitting an outer electrode terminal on a sensor element using an outer terminal installation jig;

FIG. 5 is a side view which shows an installation step of installing an outer electrode terminal on a sensor element using an outer terminal installation jig;

FIGS. 6(a), 6(b), and 6(c) show a sequence of installation steps of installing an outer electrode terminal on a sensor element;

FIGS. 6(d) and 6(e) show a sequence of installation steps of installing an inner electrode terminal on a sensor element;

FIG. 7(a) is a side view which shows an outer terminal installation jig;

FIG. 7(b) is a side view which shows an inner terminal installation jig;

FIG. 8(a) is a sectional view taken along the line A—A in FIG. 3(b);

FIG. 8(b) is a sectional view taken along the line B—B in FIG. 4(a);

FIG. 9 is a side view which shows a press device for moving press sticks to thrust an outer electrode terminal along an outer wall of an outer terminal installation jig;

FIG. 10 is a side view which shows an inner terminal installation jig fitted on a sensor element of a gas sensor which is used to install an inner electrode terminal in the sensor element;

FIGS. 11(a), 11(b), 12(a), and 12(b) show a sequence of installation steps of fitting an inner electrode terminal in a sensor element using an inner terminal installation jig;

FIGS. 13(a) and 13(b) are sectional views which show insertion of an inner electrode terminal into an opening formed in an end of a sensor element;

FIG. 14(a) is a top view which shows an inner terminal installation jig used to install an inner electrode terminal in a sensor element of a gas sensor;

FIG. 14(b) is a front view which shows an inner terminal installation jig;

FIG. 14(c) is a bottom view which shows an inner terminal installation jig;

FIG. 14(d) is a side view which shows an inner terminal installation jig;

FIG. 15(a) is a sectional view taken along the line C—C in FIG. 11(b);

FIG. 15(b) is a sectional view taken along the line D—D in FIG. 12(b);

FIGS. 16(a), and 16(b) show a sequence of installation steps of fitting an outer electrode terminal on a sensor element using an outer terminal installation jig according to the second embodiment of the invention; and FIG. 17 is a side view which shows a sensor element on which an outer electrode terminal is fitted in a manner of the second embodiment.

DESCRIPTION OF THE PREFERRED EMBODIMENTS

Figure 1:
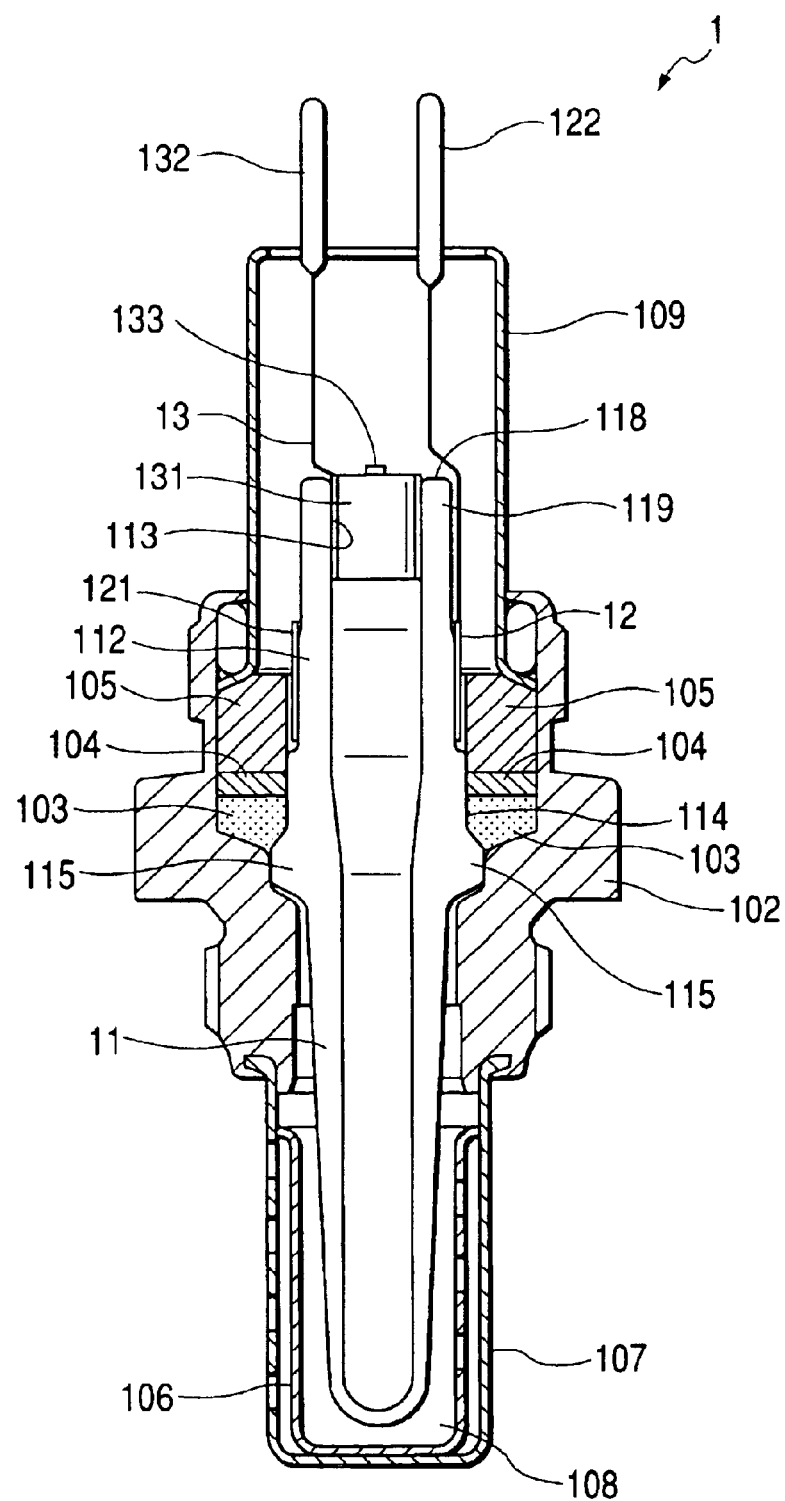
FIG. 1 is a longitudinal sectional view which shows a gas sensor capable of being assembled in a manner according to the first embodiment of the invention.

Referring to the drawings, wherein like reference numbers refer to like parts in several views, particularly to FIG. 1, there is shown a gas sensor 1 assembled in a manufacturing method according to the invention. The gas sensor 1 has, for example, a structure designed to measure the concentration of oxygen molecules contained in exhaust gasses of an automotive internal combustion engine for controlling an air-fuel ratio. The operation of this type of gas sensor is well known in the art, and explanation thereof in detail will be omitted here. For example, U.S. Pat. No. 6,222,372 B1 teaches an operation of such a type of gas sensor, disclosure of which is incorporated therein by reference.

The gas sensor 1 includes a hollow cylindrical sensor element 11 with a closed tip. The sensor element 11 has formed on an outer peripheral surface thereof an outer terminal mount 112 on which an electrode terminal 12 is mounted and on an inner peripheral surface thereof an inner terminal mount 113 to which an inner electrode terminal 13 is fitted.

Figure 2A:
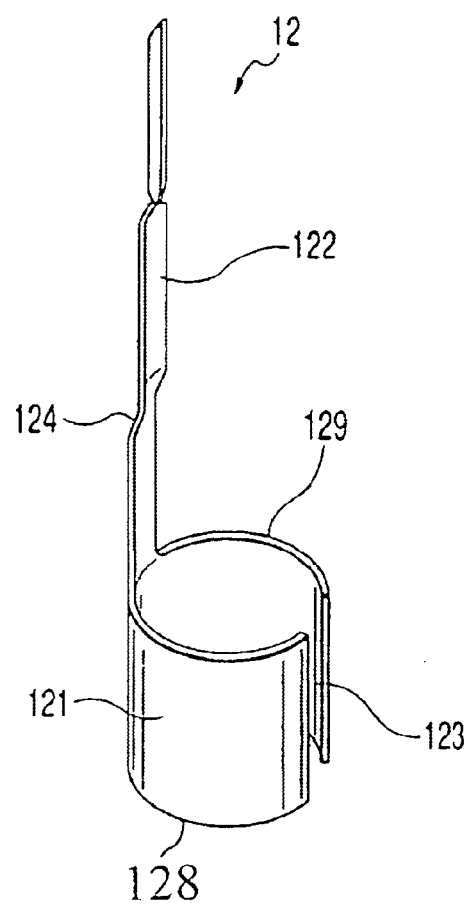
FIG. 2(a) is a perspective view which shows an outer terminal installation jig used to install an outer electrode terminal on a sensor element.

The outer electrode terminal 12, as clearly shown in FIG. 2(a) consists of an annular outer holder 121 and an outer lead 122 extending upwards, as viewed in the drawing, from an edge of the outer holder 121. The outer holder 121 is made of an elastically deformable conductive member having a given degree of elasticity and has an inner diameter smaller than an outer diameter of the outer terminal mount 112. Note that the inner diameter, as referred to in this application, is the diameter of a maximum possible circle as defined inside a cylindrical member, and the outer diameter is the diameter of a minimum possible circle as defined outside a cylindrical member.

Installation of the outer electrode terminal 12 on the sensor element 11 is, as clearly shown in FIGS. 3(a) and 3(b), accomplished in the following steps. First, an outer terminal installation jig 2 is placed in alignment with the sensor element 11 so as to face a rear end 119. The outer terminal installation jig 2 is made of a hollow cylindrical member with a skirt 21. The skirt 21, as shown in FIGS. 7(a) and 7(b), has an outer peripheral wall tapering off to the rear end 219. The front end 211 has an outer diameter greater than or equal to that of the outer terminal mount 112. The difference in outer diameter between the front end 211 of the skirt 21 and the outer terminal mount 112 is preferably within a range of 0 to 0.4 mm.

In the second step, the outer holder 121 of the outer electrode terminal 12 is, as shown in FIG. 3(b), put on the skirt 21 of the outer terminal installation jig 2.

In the third step, the outer holder 121 of the outer electrode terminal 12 is moved downward, as viewed in FIG. 3(b), along the tapered outer wall of the skirt 21 of the outer terminal installation jig 2 toward the front end 211 while expanding it, as shown in FIGS. 8(a) and 8(b) to place the outer holder 121, as shown in FIG. 4(a), around the outer terminal mount 112 of the sensor element 11.

In the fourth step, the outer terminal installation jig 2 is, as shown in FIG. 4(b), removed from the outer holder 21 leaving the outer holder 21 around the outer terminal mount 112, thereby causing the outer holder 21 to be fitted on the outer terminal mount 112 tightly in an elastic fashion. The outer electrode terminal 21 is, thus, installed on the sensor element 11 properly. After the outer holder 121 is moved along the skirt 21 to the upper edge of the annular wall 114, as viewed in FIG. 4(a), the outer holder 121 keeps a given clearance between itself and the outer surface of the outer terminal mount 112 until the outer terminal installation jig 2 is removed from the outer holder 121 completely, but however, the height of the outer holder 121 may be decreased so that the outer holder 121 establishes a tight fit on the outer terminal mount 112 immediately when the outer holder 121 is moved to the front end 211 of the skirt 21 of the outer terminal installation jig 2 and disengaged from the skirt 21.

After completion of the installation of the outer electrode terminal 12, as shown in FIGS. 6(a) to 6(c), the inner electrode terminal 13 is installed on the sensor element 11 in a manner, as shown in FIGS. 6(d) and 6(e).

Referring back to FIG. 1, the sensor element 11 on which the outer electrode terminal 12 and the inner electrode terminal 13 are installed in the above manner is disposed within a hollow cylindrical housing 102 serving as a sensor mount used in mounting the gas sensor 1, for example, in an exhaust pipe of an automotive engine. The sensor element 11 has a large-diameter portion 115 (i.e., a flange) disposed in contact with an inner wall of the housing 102. Powder 103, a pad 104, and a supporter 105 are loaded in a chamber defined by the inner wall of the housing 102 and a portion of the outer wall of the sensor element 11 above the large-diameter portion 115 and compressed for establishing an air-tight seal between the housing 102 and the sensor element 11.

The gas sensor 1 also includes a protective cover assembly and an air cover 109. The protective cover assembly consists of cup-shaped outer and inner cylinders 107 and 106 and is installed in a front end of the housing 102. The outer and inner cylinders 107 and 106 have formed therein gas holes through which a gas to be measured is admitted into a gas chamber 108 defined in the inner cylinder 106 to which a sensing portion of the sensor element 11 is exposed.

The air cover 109 is installed in a rear end of the housing 102 to cover a base portion of the sensor element 11 and defines an air chamber therein to which air is admitted as a reference gas.

The sensor element 11, as shown in FIGS. 3(a) and 1, has the inner terminal mount 113 formed on the inner wall of the rear end 119. The outer terminal mount 112 is, as described above, formed on a portion of the outer wall of the sensor element 11 closer to the tip of the sensor element 11 than the inner terminal mount 113 and has a diameter greater than that of the inner terminal mount 112. The sensor element 11 also has an annular wall 114 formed between the outer terminal mount 112 and the large-diameter portion 115 which is greater in diameter than the outer terminal mount 112 and smaller than the large-diameter portion 115.

The outer holder 121 is, as clearly shown in FIG. 4(b), fitted on the outer terminal mount 112 in contact of an end 128 with a shoulder of the annular wall 114. A rear end 129 of the outer holder 121 of the outer electrode terminal 12, as can be seen from FIG. 4(b), projects from a rear end 116 of the outer terminal mount 112 by approximately 1 mm.

The outer holder 121 of the outer electrode terminal 12 is, as clearly shown in FIG. 2(a), of a C-shape in cross section and has a slit 123. The lead 122 extends in a lengthwise direction of the sensor element 11 from a portion of the rear end 129 of the holder 121 which is diametrically opposed to the slit 123. The lead 122 has a central bend 124 extending inwardly.

The installation of the outer electrode terminal 12 on the sensor element 11 is, as shown in FIGS. 3(a) to 5, achieved by first holding the sensor element 11 using a sensor element holder 5. The sensor element holder 5 consists of a support 51 and a chuck 52 with adjustable jaws. The support 51 retains the sensor element 11 in engagement with a lower shoulder of the large-diameter portion 115. The chuck 52 holds the annular wall 114 inwardly in a radius direction.

The outer terminal installation jig 2, as shown in FIGS. 7(a) and 7(b), has the skirt 21 tapering off to the rear end 219. Specifically, a tapered portion of the skirt 21 occupies approximately three-fourths (¾) of an overall length of the skirt 21 from the rear end 219. The rest of the skirt 21 is made of a cylinder which has a constant diameter and extends straight to the front end 211.

The outer terminal installation jig 2 has formed in an inner wall thereof a cylindrical chamber or annular recess 24 in which the rear end 119 of the sensor element 11 is fitted. The inner diameter of the recess 24 is substantially identical with the outer diameter of the rear end 119 of the sensor element 11.

The installation of the outer terminal installation jig 2 on the sensor element 11 is achieved by, as shown in FIGS. 3(b) and 5, fitting the recess 24 on the rear end 119 of the sensor element 11.

The outer diameter of the front end 211 of the skirt 21 of the outer terminal installation jig 2 is, as clearly shown in FIG. 3(b), slightly greater than the outer diameter of the outer terminal mount 112 of the sensor element 11. For example, the front end 211 of the skirt 21 is greater in outer diameter than the outer terminal mount 112 by approximately 0.2 mm.

The outer diameter of the rear end 219 of the skirt 21 is less than or equal to the inner diameter of the outer holder 121 of the outer electrode terminal 12 before fitted on the outer terminal installation jig 2.

The outer terminal installation jig 2, as clearly shown in FIGS. 7(a) and 8(b), has a turn stopper 25 installed on the outer wall thereof. When the outer electrode terminal 12 is fitted on the outer terminal installation jig 2, the turn stopper 25 is disposed in the slit 123 of the outer holder 121 to avoid undesirable rotation of the outer electrode terminal 12 relative to the outer electrode terminal 12 in a circumferential direction thereof. The turn stopper 25 is, as can be seen in FIG. 7(a), mounted over approximately one-fourth (¼) of the overall length of the skirt 21 from the front end 211. FIGS. 3(a) to 5 omit the turn stopper 25 for the brevity of illustration.

The skirt 21 of the outer terminal installation jig 2, as clearly shown in FIGS. 7(a), 7(b), 8(a), and 8(b), has an outer lead guide groove 26 extending in the lengthwise direction thereof. When the outer electrode terminal 12 is fitted on the outer terminal installation jig 2, the outer lead 122 of the outer electrode terminal 12 is, as shown in FIGS. 4(a), 8(a), and 8(b), is engaged in the outer lead guide groove 26. Specifically, a portion of the outer lead 122 closer to the tip thereof than the bend 124 is engaged in the outer lead guide groove 26.

The outer terminal installation jig 2 also includes, as shown in FIGS. 3(a), 7(a), and 7(b), a central positioning pin 22 extending in alignment with a longitudinal center line of the skirt 21. The central positioning pin 22 has a tapered tip 221. When the outer terminal installation jig 2 is, as shown in FIGS. 3(a) and 3(b), fitted on the rear end 119 of the sensor element 11, the central positioning pin 22 is inserted into the rear end 119 to secure the alignment of the outer terminal installation jig 2 with the sensor element 11.

The thrusting of the outer holder 121 of the outer electrode terminal 112 along the skirt 21 of the outer terminal installation jig 2 toward the front end 211 is accomplished by pushing, as shown in FIGS. 3(b), 4(a), 8(a), and 8(b), two sticks 42 against diametrically opposed portions of the rear end 129 of the outer holder 121. Each of the sticks 42 has, as shown in FIGS. 8(a), 8(b), and 9, a reinforcement 422 installed on a central portion thereof in a widthwise direction which has a greater thickness.

The sticks 42 are, as clearly shown in FIG. 9, retained by a stick holder 40. The stick holder 40 consists of a base 401 and a pair of stick mounts 402. The sticks 42 are installed on the stick mounts 402. The stick mounts 402 are installed on the base 401 pivotably about pins 403 and urged elastically by springs 404 in an inward direction. Specifically, the springs 404 are provided between the base 401 and the stick mounts 402 to elastically urge the sticks 42 inwardly to bring tips 21 close to each other, as indicated by arrows F in FIG. 9.

The skirt 21 of the outer terminal installation jig 2, as shown in FIGS. 7(a) and 7(b), has two slide guide grooves 23 formed diametrically in the outer wall thereof. The slide guide grooves 23 extend in the lengthwise direction of the skirt 21 and work to guide sliding movement of the sticks 42. Specifically, as shown in FIGS. 3(b), 4(a), 8(a), and 8(b), when the outer electrode terminal 12 is thrust along the skirt 21 of the outer terminal installation jig 2, the sticks 42 are engaged in the slide guide grooves 23 and pushed against the outer holder 121 of the outer electrode terminal 12, thereby moving the outer holder 121 toward the front end 211 of the skirt 21.

The two slide guide grooves 23 are, as described above, diametrically opposed to each other. The two sticks 42 are, as already described, elastically urged to bring the tips 421 close to each other. This causes the tips 421 of the sticks 42 to be pressed slightly against bottoms of the slide guide grooves 23 and moved along the slide guide grooves 23.

Next, the installation of the inner electrode terminal 13 on the sensor element 11 will be described below.

Figure 2B:
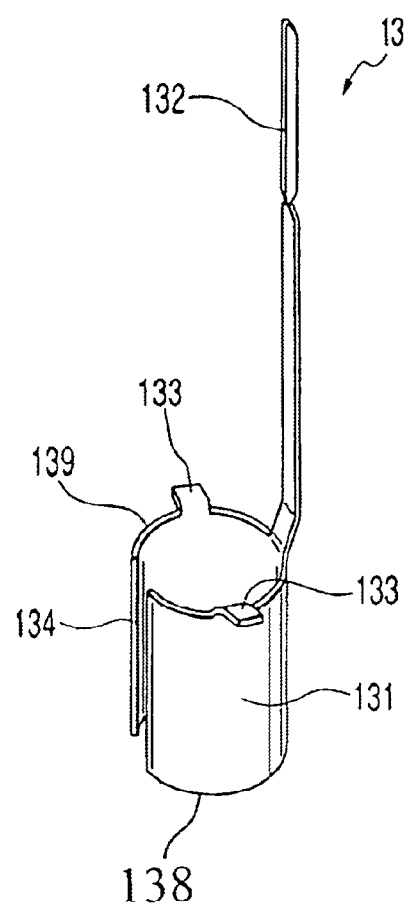
FIG. 2(b) is a perspective view which shows an inner terminal installation jig used to install an inner electrode terminal in a sensor element.

The inner electrode terminal 13, as shown in FIG. 2(b), consists of an inner holder 131 and an inner lead 132. The inner lead 132 extends from an edge of the inner holder 131 in the lengthwise direction of the sensor element 11. The inner holder 131 has protrusions or tabs 133 which are formed on diametrically opposed portions of a rear end 139 and extend outward.

The inner holder 131 has the outer diameter greater than the inner diameter of the inner electrode mount 113 of the sensor element 11 before the inner holder 131 is fitted in the sensor element 11 and has a given degree of elasticity. The inner holder 131 is, as clearly shown in FIG. 2(b), of a C-shape in cross section and has a slit 134. The inner lead 132 extends in the lengthwise direction of the sensor element 11 from a portion of the rear end 139 of the holder 131 which is diametrically opposed to the slit 134. The lead 132 has a central bend 135 extending outward.

The tabs 133 work as a stopper to avoid excessive insertion of the inner holder 131 into the inner terminal mount 113 of the sensor element 11.

The installation of the inner electrode terminal 13 into the inner terminal mount 113 of the sensor element 11 is, as shown in FIGS. 6(d), 6(e), 12, and 13, achieved by inserting the inner holder 131 from the rear end 119 of the sensor element 11. The insertion of the inner holder 131 is arrested when a given clearance is created between each of the tabs 133 and the rear end surface 118 of the sensor element 11. The clearance between the tabs 133 and the rear end surface 118 of the sensor element 11 is preferably within a range of 0.2 to 0.5 mm, and more preferably approximately 0.3 mm.

Specifically, the installation of the inner electrode terminal 13 into the inner terminal mount 113 of the sensor element 11 is, as shown in FIGS. 10, 11(a), and 11(b), accomplished in the following steps. First, an inner terminal installation jig 3 is disposed on the rear end 119 of the sensor element 11. The inner terminal installation jig 3 has formed therein a central through hole 31 which has, as can be seen from FIGS. 10 to 14(d), an inner wall tapering off toward a front end opening 311 from a rear end opening 319. The diameter of the front end opening 311 is, as can be seen in FIG. 11(b), less than or equal to the inner diameter of the inner terminal mount 113 of the sensor element 11.

The contour of the hole 31, as illustrated in FIGS. 10 to 12(b), represents a maximum cylindrical space within which the inner holder 131 can be fitted, not an inner wall thereof (see FIGS. 15(a) and 15(b)).

In the second step, the inner holder 131 of the inner electrode terminal 13 is, as shown in FIG. 11(b), inserted into the through hole 31 from the rear end opening 319 of the inner terminal installation jig 3.

In the third step, a stick 43, as shown in FIGS. 10, 11(b), and 12(a), is abutted at a tip 431 thereof to diametrically opposed portions of the rear end 139 of the inner holder 131 to thrust the inner holder 131 toward the front end opening 311 of the through hole 31 while decreasing the diameter of the inner holder 131, as shown in FIGS. 15(a) and 15(b) until the inner holder 131 is, as shown in FIG. 12(b), in a press fit within the inner terminal mount 113.

In the fourth step, the inner terminal installation jig 3 is removed from the inner holder 131. The inner electrode terminal 13 is, thus, installed in the sensor element 11, as shown in FIGS. 6(e) and 13(b).

The inner terminal installation jig 3 has, as described above, formed therein the through hole 31 with the tapered wall. The inner terminal installation jig 3 has formed in a central end thereof an annular chamber 34 which leads to the hole 31 through a front end opening 311 and within which the rear end 119 of the sensor element 11 is fitted when the inner electrode terminal 13 is installed in the sensor element 11.

The diameter of the front end opening 311 of the through hole 31 is, as shown in FIG. 11(b), less than or equal to that of the inner terminal mount 113 of the sensor element 11. Specifically, the front end opening 311 is smaller in diameter than the inner terminal mount 113 by approximately 0.2 mm.

The diameter of a rear end opening 391 of the hole 31 is greater than or equal to the outer diameter of the inner holder 131 of the inner electrode terminal 13 before installed in the sensor element 11.

The through hole 31 is, as clearly shown in FIGS. 15(a) and 15(b), of a cross-shape in section. The distance d between two of four inner corners diametrically opposed to each other: corners 31a and 31b decreases at a given rate as approaching the front end opening 311 from the rear end opening 319. The diameter d is, however as shown in FIGS. 14(b) and 14(d), kept constant between the middle between the rear end opening 319 and the front end opening 311 and the front end opening 311.

The diameters of the rear end opening 319 and the front end opening 311 are given by values of the distances d thereat, respectively.

The through hole 31, as shown in FIGS. 14(a), 14(b), 14(c), 15(a), and 15(b), has an inner lead guide groove 35 which extends straight in the lengthwise direction of the through hole 31 and within which the inner lead 132 of the inner electrode terminal 13 is, as shown in FIGS. 10, 12(a), 15(a), and 15(b), disposed when the inner electrode terminal 13 is installed in the sensor element 11.

The through hole 31, as shown in FIGS. 14(a), 14(c), 14(d), 15(a), and 15(b), also has two slide guide grooves 33 which are formed in diametrically opposed inner walls of the inner terminal installation jig 3 and work to guide sliding movement of the stick 43 when forcing the inner holder 131 into the inner terminal mount 113 through the through hole 31.

The stick 43 is implemented by a strip member having the width greater than the diameter of the inner holder 131 of the inner electrode terminal 13 before installed in the sensor element 11.

The inner slide guide grooves 33, as can be seen in FIGS. 15(a) and 15(b), also work to guide sliding movement of the tabs 133 of the inner electrode terminal 13 when the inner holder 131 is moved through the through hole 31.

The through hole 31, as shown in FIGS. 14(a), 14(b), and 14(c), also has an outer lead storage groove 36 which is formed in an inner wall of the inner terminal installation jig 3 diametrically opposed to the inner lead guide groove 35 and within which the outer lead 122 of the outer electrode terminal 12 is, as shown in FIGS. 10 to 12(b), 15(a), and 15(b), disposed when the inner terminal installation jig 3 is installed on the rear end 119 of the sensor element 11 after the outer electrode terminal 12 is installed for avoiding physical interference of the inner terminal installation jig 3 with the outer lead 122.

The installation of the outer electrode terminal 12 in the sensor element 11 is accomplished, as described above, by moving the outer holder 121 of the outer electrode terminal 12 along the skirt 21 of the outer terminal installation jig 2 toward the front end 211 while increasing the diameter of the outer holder 121, thereby fitting the inner holder 121 on the outer terminal mount 112 of the sensor element 11 (see FIGS. 3(b), 4(a), and 4(b)). The skirt 21 has, as described above, the tapered wall and has the outer diameter at the front end 211 which is greater than or equal to the outer diameter of the outer terminal mount 112. This causes the inner diameter of the outer holder 121 to increase up to the outer diameter of the outer terminal mount 112 or more when the outer holder 121 has reached the front end 211 of the outer terminal installation jig 2. Specifically, the outer holder 121 is increased in the inner diameter to the outer diameter of the outer terminal mount 112 or more and fitted, as shown in FIG. 4(a), on the outer terminal mount 112 without interfering the rear end 119 of the sensor element 11 physically, which minimizes the possibility of physical damage to the sensor element 11. Additionally, the use of the skirt 21 facilitates ease of increasing the diameter of the outer holder 121 when mounted on the outer terminal mount 112, thus resulting in improved productivity of the gas sensor 1.

The installation of the inner electrode terminal 13, as described above, follows the installation of the outer electrode terminal 12 on the sensor element 11. This facilitates ease of the installation of the outer electrode terminal 12 on the sensor element 11. Specifically, if the outer electrode terminal 12 is installed on the gas sensor 11 after completion of installation of the inner electrode terminal 13, the inner electrode terminal 13 interferes with the installation of the outer electrode terminal 12. In practice, the lead 132 of the inner electrode terminal 13 projecting from the rear end 119 of the sensor element 11 results in difficulty in mounting the outer terminal installation jig 2 on the sensor element 11. The assembling method of this embodiment, however, does not suffer from this problem.

The use of the central positioning pin 22 of the outer terminal installation jig 2 secures the stability of alignment of the outer terminal installation jig 2 with the sensor element 11 when the outer terminal installation jig 2 is fitted on the rear end 119 of the sensor element 11. This avoids the physical interference of the outer holder 121 with the rear end 119 when the outer electrode terminal 12 is installed on the sensor element 11, thus minimizing the damage to the outer electrode terminal 12.

The insertion of the inner holder 131 of the inner electrode terminal 13 into the inner terminal mount 113 is arrested, as described above in FIG. 13(b), when a given gap is formed between the tabs 133 and the rear end surface 118 of the sensor element 11, thereby eliminating the possibility of the tab 113 causing damage to the sensor element 11.

The sliding movement of the outer electrode terminal 12 along the skirt 21 of the outer terminal installation jig 2 is, as described above in FIGS. 3(b), 4(a), 8(a), and 8(b), achieved by pressing the diametrically opposed portions of the rear end 129 of the outer holder 121 using the sticks 42. This provides for ease of the sliding movement of the outer electrode terminal 12 and ensures desired horizontal orientation of the outer electrode terminal 12 relative to the rear end 119 of the sensor element 11.

The skirt 21, as described above in FIGS. 7(a) and 7(b), has the two slide guide grooves 23 formed diametrically in the outer wall thereof. The slide guide grooves 23 work to guide sliding movement of the sticks 42 when forcing, as shown in FIGS. 3(b) and 4(a), the outer holder 121 to the front end 211 of the skirt 21. The use of the slide guide grooves 23 ensures the stability of contact of the sticks 42 with the rear end 129 of the outer holder 121, thus facilitating ease of pushing the outer holder 121.

The outer terminal installation jig 2 has formed in the inner wall thereof the annular recess 24 within which the rear end 119 of the sensor element 11 is fitted. The inner diameter of the recess 24 is substantially identical with the outer diameter of the rear end 119 of the sensor element 11. This establishes a fine fit of the outer terminal installation jig 2 with the sensor element 11 and ensures a desirable positional relation between the outer terminal installation jig 2 and the sensor element 11.

The outer terminal installation jig 2, as described above in FIGS. 7(a) and 8(b), has the turn stopper 25 which is disposed in the slit 123 of the outer holder 121 when the outer electrode terminal 12 is fitted on the outer terminal installation jig 2, thereby avoiding undesirable rotation of the outer electrode terminal 12 relative to the outer electrode terminal 12 in the circumferential direction thereof.

The skirt 21 of the outer terminal installation jig 2, as described above in FIGS. 7(a), 7(b), 8(a), and 8(b), has the outer lead guide groove 26 extending in the lengthwise direction thereof. When the outer electrode terminal 12 is fitted on the outer terminal installation jig 2, the outer lead 122 of the outer electrode terminal 12 is, as shown in FIGS. 4(a), 8(a), and 8(b), is engaged in the outer lead guide groove 26, thereby avoiding deformation of the outer lead 122 caused by undesirable contact of the outer lead 122 with the surface of the skirt 21.

The installation of inner electrode terminal 13 into inner terminal mount 113 of sensor element 11 is, as described above in FIGS. 6(d), 6(e), 12, and 13, achieved by moving the inner bolder 131 of inner electrode terminal 13 along the tapered wall of through hole 31 of inner terminal installation jig 3 to decrease the diameter of inner holder 131 below the inner diameter of inner terminal mount 113, thereby allowing inner holder 131 to be inserted into the inner terminal mount 113 of sensor element 11 without interfering with rear end 119 physically, which eliminates damage to sensor element 11.

The through hole 31, as described in FIGS. 14(a), 14(c), 14(d), 15(a), and 15(b), has the two slide guide grooves 33 within which the stick 43 is engaged when forcing the inner holder 131 into the inner terminal mount 113. The use of the slide guide grooves 33 ensures the stability of the sliding movement of the stick 43 through the hole 31, thus facilitating ease of pushing the inner holder 131 along the hole 31.

The inner terminal installation jig 3 has formed in the inner wall thereof the annular recess 34 within which the rear end 119 of the sensor element 11 is fitted. The inner diameter of the recess 34 may be substantially identical with the outer diameter of the rear end 119 of the sensor element 11. This establishes a fine fit of the inner terminal installation jig 3 with the sensor element 11 and ensures a desirable positional relation between the inner terminal installation jig 3 and the sensor element 11.

The through hole 31, as described above in FIGS. 14(a), 14(b), 14(c), 15(a), and 15(b), has the inner lead guide groove 35 which extends straight in the lengthwise direction of the through hole 31 and within which the inner lead 132 of the inner electrode terminal 13 is, as shown in FIGS. 10, 12(a), 15(a), and 15(b), disposed when the inner electrode terminal 13 is installed in the sensor element 11. The use of the inner lead guide groove 35 avoids deformation of the inner lead 132 caused by undesirable physical contact with the inner wall of the through hole 31.

The through hole 31, as described above in FIGS. 14(a), 14(c), 14(d), 15(a), and 15(b), also has the two slide guide grooves 33 which work to guide sliding movement of the stick 43 when forcing the inner holder 131 into the inner terminal mount 113 through the through hole 31. The slide guide grooves 33 also work as chambers within which the tabs 133 of the inner electrode terminal 13 are disposed when the inner holder 131 is moved through the through hole 31, thereby avoiding undesirable deformation of the tabs 133 caused by the physical contact of the tabs 133 with the inner wall of the inner terminal installation jig 3.

The through hole 31, as described above in FIGS. 14(a), 14(b), 14(c), also has the outer lead storage groove 36 within which the outer lead 122 of the outer electrode terminal 12 is, as shown in FIGS. 10 to 12(b), 15(a), and 15(b), disposed when the inner terminal installation jig 3 is installed on the rear end 119 of the sensor element 11 after the outer electrode terminal 12 is installed. This enables the installation of the inner electrode terminal 13 in the sensor element 11 without undesirable physical contact with the outer electrode terminal 12 already installed in the sensor element 11.

FIGS. 16(a), 16(b), and 17 show the gas sensor production method according to the second embodiment of the invention in which the outer electrode terminal 12 is fitted on the outer terminal mount 112 formed on the periphery of the rear end 119 of a sensor element 110 different in structure from the sensor element 11 of the first embodiment.

The sensor element 110 has the outer terminal mount 112 formed on the periphery of the rear end 119. The sensor element 110, like the first embodiment, also has the annular wall 114 and the large-diameter portion 115 formed on the front side of the outer terminal mount 112.

The installation of the outer electrode terminal 12 on the sensor element 11 is accomplished using an outer terminal installation jig 20. The outer terminal installation jig 20, like the outer terminal installation jig 2 of the first embodiment, consists of the skirt 21 and the central positioning pin 22. The central positioning pin 22 extends along the longitudinal center line of the outer terminal installation jig 20 and is inserted into the rear end 119 of the sensor element 110 to establish alignment of the outer terminal installation jig 20 with the sensor element 11.

The outer diameter of the front end 211 of the skirt 21 is greater than or equal to the outer diameter of the outer terminal mount 112 of the sensor element 110. The outer diameter of the rear end 219 of the skirt 21 is smaller than or equal to the inner diameter of the outer holder 121 of the outer electrode terminal 12 before installed on the sensor element 110.

The outer terminal installation jig 20, as clearly shown in FIG. 16(a), has no annular chamber such as the one as indicated by numeral 24 in FIG. 3(a).

The outer diameter of the central positioning pin 22 is substantially equal to the inner diameter of the rear end 119 of the sensor element 110. Specifically, the outer diameter of the central positioning pin 22 is greater than the inner diameter of the rear end 119 by approximately 0.05 mm to establish a press fit within the rear end 119, thereby ensuring accurate alignment of the longitudinal center line of the outer terminal installation jig 20 with that of the sensor element 110. This further minimizes the possibility of undesirable physical contact of the outer holder 121 of the outer electrode terminal 12 with the rear end 119 of the sensor element 110 when the outer holder 121 is fitted on the outer terminal mount 112.

The installation of the outer electrode terminal 12 on the sensor element 110 is accomplished in the following steps. First, the outer terminal installation jig 20 is, as shown in FIG. 16(a), placed in alignment with the rear end 119 of the sensor element 110.

Next, the central positioning pin 22 is, as shown in FIG. 16(b), inserted into the rear end 119 of the sensor element 110, bringing the front end 211 of the skirt 21 into direct contact with the rear end 119 of the sensor element 110. Subsequently, the outer electrode terminal 12 is moved along the skirt 21 and fitted on the outer terminal mount 112 of the sensor element 110 in the same manner as described in the first embodiment. Finally, the outer terminal installation jig 20 is removed from the outer holder 21 of the outer electrode terminal 21.

Other arrangements are identical with those in the first embodiment, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A method for manufacturing a gas sensor that includes (a) a hollow cylindrical sensor element having a first and a second end portion axially opposed to each other and (b) an inner electrode terminal installed on an inner terminal mount formed on an inner peripheral surface of the second end portion of the cylindrical sensor element, said method comprising:

preparing the inner electrode terminal as an elastically deformable annular holder, a lead, and a protrusion, the annular holder having an outer diameter greater than an inner diameter of the inner terminal mount of the cylindrical sensor element and a first and a second end axially opposed to each other, the lead extending axially from the second end of the annular holder, the protrusion projecting from the second end of the annular holder radially outward; and inserting the annular holder of the inner electrode terminal at the first end thereof into the second end portion of the cylindrical sensor element until a given clearance is formed between the protrusion and an end surface of the second end portion of the cylindrical sensor element to install the inner electrode terminal on the inner terminal mount of the sensor element.

2. A method for manufacturing a gas sensor that includes (a) a hollow cylindrical sensor element having a first and a second end portion axially opposed to each other, (b) an outer electrode terminal installed on an outer terminal mount formed on an outer peripheral surface of the second end portion of the cylindrical sensor element, and (c) an inner electrode terminal installed on an inner terminal mount formed on an inner peripheral surface of the second end portion of the cylindrical sensor element, said method comprising:

preparing the outer electrode terminal as an elastically deformable annular holder with a lead extending therefrom, the annular holder having an inner diameter smaller than an outer diameter of said outer terminal mount;

placing an outer terminal installation jig on the second end portion of the sensor element, said outer terminal installation jig having a first and a second end axially opposed to each other and a skirt with an outer wall tapering off to the second end, an outer diameter of the first end being greater than or equal to the outer diameter of the outer terminal mount of the sensor element, the first end of said outer terminal installation jig being placed on the second end portion of the sensor element;

placing the annular holder of the outer electrode terminal on the skirt of the outer terminal installation jig;

moving the annular holder toward the first end of the outer installation terminal jig along the tapered outer wall of the skirt to increase the inner diameter of the annular holder and place the annular holder at the outer terminal mount of the sensor element;

removing the outer terminal installation jig from the annular holder of the outer electrode terminal to establish tight engagement of the annular holder with the outer terminal mount of the sensor element; and subsequently installing the inner electrode terminal on the inner terminal mount, wherein said outer terminal installation jig includes a central positioning pin which is disposed in the skirt along a longitudinal center line of the skirt and partially projects from the first end of said outer terminal installation jig, and wherein placing of said outer terminal installation jig includes inserting the central positioning pin into the second end portion of the sensor element to align said outer terminal installation jig with the sensor element.

3. A method for manufacturing a gas sensor that includes (a) a hollow cylindrical sensor element having a first and a second end portion axially opposed to each other and (b) an outer electrode terminal installed on an outer terminal mount formed on an outer peripheral surface of the second end portion of the cylindrical sensor element, said method comprising:

preparing the outer electrode terminal as an elastically deformable annular holder having a first and a second end axially opposed to each other with a lead extending from the second end of the annular holder, the annular holder having an inner diameter smaller than an outer diameter of the outer terminal mount of the cylindrical sensor element;

placing an outer terminal installation jig on the second end portion of the sensor element, said outer terminal installation jig having a first and a second end axially opposed to each other and a skirt with an outer wall tapering off to the second end, an outer diameter of the first end being greater than or equal to the outer diameter of the outer terminal mount of the sensor element, the first end of said outer terminal installation jig being placed on the second end portion of the sensor element;

placing the annular holder of the outer electrode terminal on the skirt of the outer terminal installation jig;

placing press members in contact with a plurality of portions of the second end of the annular holder of the outer electrode terminal;

thrusting the press members toward the first end of the outer installation terminal jig to move the annular holder of the outer electrode terminal along the tapered outer wall of the skirt to increase the inner diameter of the annular holder and place the annular holder at the outer terminal mount of the sensor element;

removing the outer terminal installation jig from the annular holder of the outer electrode terminal to establish tight engagement of the annular holder with the outer terminal mount of the sensor element; and wherein the skirt of the outer terminal installation jig has a plurality of slide guide grooves formed in an outer surface thereof which extend in a lengthwise direction of the outer terminal installation jig to guide sliding movement of the press members to thrust the annular holder of the outer electrode terminal to the first end from the second end of the outer terminal installation jig.

4. A method as in claim 3, wherein:

said outer terminal installation jig includes a central positioning pin which is disposed in the skirt along a longitudinal center line of the skirt and partially projects from the first end of said outer terminal installation jig, and said placing of the outer terminal installation jig includes inserting the central positioning pin into the second end portion of the sensor element to align said outer terminal installation jig with the sensor element.

5. A method for manufacturing a gas sensor which includes (a) a hollow cylindrical sensor element having a first and a second end portion axially opposed to each other and (b) an inner electrode terminal installed on an inner terminal mount formed on an inner peripheral surface of the second end portion of the cylindrical sensor element, said method comprising:

preparing the inner electrode terminal as an elastically deformable annular holder with a lead, the annular holder having an outer diameter greater than an inner diameter of the inner terminal mount of the cylindrical sensor element and a first and a second end axially opposed to each other, the lead extending from the second end of the annular holder;

placing an inner terminal installation jig on the second end portion of the sensor element, said inner terminal installation jig having a first and a second end axially opposed to each other and a through hole tapering off to the first end, an inner diameter of an opening of the through hole formed in the first end being smaller than or equal to the inner diameter of the inner terminal mount of the sensor element; the first end of said inner terminal installation jig being placed on the second end portion of the sensor element;

placing the annular holder of the inner electrode terminal in the through hole of the inner terminal installation jig;

placing at least one press member in contact with a plurality of portions of the second end of the annular holder of the inner electrode terminal;

thrusting the at least one press members toward the first end of the inner installation terminal jig to move the annular holder of the inner electrode terminal through the through hole to decrease the outer diameter of the annular holder and place the annular holder at the inner terminal mount of the sensor element;

removing the inner terminal installation jig from the annular holder of the inner electrode terminal to establish tight engagement of the annular holder with the inner terminal mount of the sensor element; and wherein the inner terminal installation jig has a plurality of slide guide grooves formed in an inner surface thereof which extend in a lengthwise direction of the inner terminal installation jig to guide sliding movement of the at least one press member to thrust the annular holder of the inner electrode terminal to the first end from the second end of the inner terminal installation jig.

6. A method as in claim 5, wherein:

the inner electrode terminal has a protrusion projecting from the second end of the annular holder radially outward, and said thrusting step moves the annular holder of the inner electrode terminal through the through hole until a given clearance is formed between the protrusion and an end surface of the second end portion of the cylindrical sensor element to install the inner electrode terminal on the inner terminal mount of the sensor element.

7. A method for manufacturing a gas sensor that includes (a) a hollow cylindrical sensor element having a first and a second end portion axially opposed to each other, (b) an outer electrode terminal installed on an outer terminal mount formed on an outer peripheral surface of the second end portion of the cylindrical sensor element, and (c) an inner electrode terminal installed on an inner terminal mount formed on an inner peripheral surface of the second end portion of the cylindrical sensor element, said method comprising:

preparing the outer electrode terminal as an elastically deformable annular holder with a lead extending therefrom, the annular holder having an inner diameter smaller than an outer diameter of said outer terminal mount;

placing an outer terminal installation jig on the second end portion of the sensor element, said outer terminal installation jig having a first and a second end axially opposed to each other and a skirt with an outer wall tapering off to the second end, an outer diameter of the first end being greater than or equal to the outer diameter of the outer terminal mount of the sensor element at the first end of said outer terminal installation jig being placed on the second end portion of the sensor element;

placing the annular holder of the outer electrode terminal on the skirt of the outer terminal installation jig;

placing press members in contact with a plurality of portions of the second end of the annular holder of the outer electrode terminal;

thrusting the press members toward the first end of the outer installation terminal jig to move the annular holder of the outer electrode terminal along the tapered outer wall of the skirt to increase the inner diameter of the annular holder and place the annular holder at the outer terminal mount of the sensor element;

removing the outer terminal installation jig from the annular holder of the outer electrode terminal to establish tight engagement of the annular holder with the outer terminal mount of the sensor element;

preparing the inner electrode terminal as an elastically deformable annular holder, a lead, and a protrusion, the annular holder having an outer diameter greater than an inner diameter of the inner terminal mount of the cylindrical sensor element and a first and a second end axially opposed to each other, the lead extending from the second end of the annular holder, the protrusion projection radially from the second end of the annular holder outward;

after removing the outer terminal installation jig, placing an inner terminal installation jig on the second end portion of the sensor element, said inner terminal installation jig having a first and a second end axially opposed to each other and a through hole tapering off to the first end, an inner diameter of an opening of the through hole formed in the first end being smaller than or equal to the inner diameter of the inner terminal mount of the sensor element, the first end of the inner terminal installation jig being placed on the second end portion of the sensor element;

placing the annular holder of the inner electrode terminal in the through hole of the inner terminal installation jig;

placing press at least one members in contact with a plurality of portions of the second end of the annular holder of the inner electrode terminal;

thrusting the at least one press members toward the first end of the inner installation terminal jig to move the annular holder of the inner electrode terminal through the through hole to decrease the outer diameter of the annular holder and place the annular holder at the inner terminal mount of the sensor element; and removing the inner terminal installation jig from the annular holder of the inner electrode terminal to establish tight engagement of the annular holder with the inner terminal mount of the sensor element.

* * * * *